US011243391B2

(12) United States Patent
Hillman

(10) Patent No.: US 11,243,391 B2
(45) Date of Patent: Feb. 8, 2022

(54) THREE-DIMENSIONAL IMAGING USING SWEPT CONFOCALLY ALIGNED PLANAR EXCITATION WITH ASYMMETRICAL MAGNIFICATION

(71) Applicant: The Trustees of Columbia University in the City of New York, New York, NY (US)

(72) Inventor: Elizabeth M. C. Hillman, New York, NY (US)

(73) Assignee: The Trustees of Columbia University in the City of New York, New York, NY (US)

(*) Notice: Subject to any disclaimer, the term of this patent is extended or adjusted under 35 U.S.C. 154(b) by 740 days.

(21) Appl. No.: 16/303,017

(22) PCT Filed: May 30, 2017

(86) PCT No.: PCT/US2017/034945
§ 371 (c)(1),
(2) Date: Nov. 19, 2018

(87) PCT Pub. No.: WO2017/210159
PCT Pub. Date: Dec. 7, 2017

(65) Prior Publication Data
US 2019/0317312 A1    Oct. 17, 2019

Related U.S. Application Data

(60) Provisional application No. 62/402,011, filed on Sep. 30, 2016, provisional application No. 62/343,103, filed on May 30, 2016.

(51) Int. Cl.
*A61B 3/10* (2006.01)
*A61B 3/14* (2006.01)
(Continued)

(52) U.S. Cl.
CPC .......... *G02B 21/367* (2013.01); *A61B 3/1025* (2013.01); *A61B 3/14* (2013.01);
(Continued)

(58) Field of Classification Search
CPC .... A61B 3/1025; A61B 3/14; G02B 21/0032; G02B 21/0048; G02B 21/0052;
(Continued)

(56) References Cited

U.S. PATENT DOCUMENTS 4,826,299 A   5/1989  Powell
5,266,803 A   11/1993 Heffelfinger
(Continued)

FOREIGN PATENT DOCUMENTS

WO   2003012517 A2   2/2003
WO   2015109323 A2   7/2015
(Continued)

OTHER PUBLICATIONS

Extended European Search Report dated Jan. 27, 2020 for European Patent Application No. 17807317.7.
(Continued)

*Primary Examiner* — Ryan S Dunning
(74) *Attorney, Agent, or Firm* — Potomac Law Group, PLLC

(57) ABSTRACT

Implementing swept, confocally aligned planar excitation (SCAPE) imaging with asymmetric magnification in the detection arm provides a number of significant advantages. In some preferred embodiments, the asymmetric magnification is achieved using cylindrical lenses in the detection arm that are oriented to increase the magnification of the intermediate image in the width direction but not in the depth direction. SCAPE imaging may also be improved by using an SLM to modify a characteristic of the sheet of excitation light that is projected into the sample. Additional
(Continued)

embodiments include a customized version of SCAPE that is optimized for imaging the retina at the back of an eyeball in living subjects.

21 Claims, 11 Drawing Sheets

(51) Int. Cl.
  *G02B 21/00* (2006.01)
  *G02B 21/36* (2006.01)
  *H04N 5/232* (2006.01)

(52) U.S. Cl.
  CPC ..... *G02B 21/0032* (2013.01); *G02B 21/0048* (2013.01); *G02B 21/0076* (2013.01); *H04N 5/23296* (2013.01); *G02B 21/006* (2013.01); *G02B 21/0052* (2013.01); *G02B 21/0072* (2013.01)

(58) Field of Classification Search
  CPC .............. G02B 21/006; G02B 21/0072; G02B 21/0076; G02B 21/361; G02B 21/367; H04N 5/23296
  See application file for complete search history.

(56) References Cited

U.S. PATENT DOCUMENTS

| | | | |
|---|---|---|---|
| 5,485,530 | A | 1/1996 | Lakowicz et al. |
| 7,710,115 | B2 | 5/2010 | Hargreaves |
| 8,254,020 | B2 | 8/2012 | Holy et al. |
| 8,290,358 | B1 | 10/2012 | Georgiev |
| 8,441,633 | B2 | 5/2013 | Truong et al. |
| 8,575,570 | B2 | 11/2013 | Choi et al. |
| 8,619,237 | B2 | 12/2013 | Hillman et al. |
| 8,679,426 | B2 | 3/2014 | Barrett |
| 8,718,351 | B2 | 5/2014 | So et al. |
| 8,884,211 | B2 * | 11/2014 | Feng .................. G01N 21/6456 250/234 |
| 9,357,202 | B2 | 5/2016 | Pavani et al. |
| 9,655,523 | B2 | 5/2017 | Hillman et al. |
| 10,061,111 | B2 | 8/2018 | Hillman |
| 2003/0142934 | A1 | 7/2003 | Pan et al. |
| 2010/0090127 | A1 | 4/2010 | Yekta et al. |
| 2010/0214404 | A1 | 8/2010 | Chen et al. |
| 2012/0140240 | A1 | 6/2012 | Hillman et al. |
| 2012/0281264 | A1 | 11/2012 | Lippert et al. |
| 2014/0146376 | A1 | 5/2014 | Kleppe et al. |
| 2015/0042992 | A1 | 2/2015 | Cui et al. |
| 2016/0213252 | A1 | 7/2016 | Hillman et al. |
| 2018/0214024 | A1 | 8/2018 | Hillman et al. |

FOREIGN PATENT DOCUMENTS

| | | |
|---|---|---|
| WO | 2017210182 A1 | 12/2017 |
| WO | 2018013489 A1 | 1/2018 |
| WO | 2018050888 A1 | 3/2018 |
| WO | 2018052905 A1 | 3/2018 |
| WO | 2018064149 A1 | 4/2018 |
| WO | 2018069170 A1 | 4/2018 |
| WO | 2018089865 A1 | 5/2018 |

OTHER PUBLICATIONS

Ahrens et al., "Whole-brain functional imaging at cellular resolution using lightsheet microscopy", Nature Methods, Mar. 18, 2013, vol. 10(5): p. 413-420 (Abstract).

Bouchard et al., "Swept confocally-aligned planar excitation (SCAPE) microscopy for high-speed volumetric imaging of behaving organisms," Nature Photonics, Jan. 19, 2015, vol. 9(2), pp. 113-119.

Dean et al., "Deconvolution-free Subcellular Imaging with Axially Swept Light Sheet Microscopy" Biophysics Journal, vol. 108, Issue 12, pp. 2807-2815, Jun. 2015.

Dmitriev et al., "Optical probes and techniques for O2 measurement in live cells and tissue", Cellular and Molecular Life Sciences, vol. 69, Issue 12, pp. 2025-2039, Jun. 2012.

Dodt et al., "Ultramicroscopy: development and outlook," Neurophotonics, Nov. 9, 2015, vol. 2(4), pp. 041407-1-041407-8.

Holekamp et al., "Fast Three-Dimensional Fluorescence Imaging of Activity in Neural Populations by Objective-Coupled Planar Illumination Microscopy", Neuron, Mar. 13, 2008, vol. 57, pp. 661-672.

International Search Report and Written Opinion for Application No. PCT/US2017/053687 dated Feb. 13, 2018.

International Search Report and Written Opinion for International Application No. PCT/US2017/034945 dated Aug. 23, 2017.

Jahn et al., "Simultaneous Fluorescence and Phosphorescence Lifetime Imaging Microscopy in Living Cells", Scientific Reports, 5:14334, Sep. 2015.

Kepshire et al., "A microcomputed tomography guided fluorescence tomography system for small animal molecular imaging", Review of Scientific Instruments, vol. 80, Issue 4, p. 043701, Apr. 2009.

Lecoq et al., "Simultaneous two-photon imaging of oxygen and blood flow in deep cerebral vessels", Nature Medicine, vol. 17, Issue 7, pp. 893-899, Jul. 2011.

Olarte et al., "Decoupled illumination detection in light sheet microscopy for fast volumetric imaging," Optica, Aug. 4, 2015, vol. 2, No. 8, p. 702-705.

Ploschner et al., "Multimode fibre: Light-sheet microscopy at the tip of a needle", Scientific Reports, 5:18050, Dec. 2015.

Powell, "About the Powell Lens," retrieved from the Internet: http://www.laserlineoptics.com/powell_primer.html, retrieved on Nov. 24, 2017, pp. 1-4.

Prevedel et al., "Simultaneous whole-animal 3D imaging of neuronal activity using light-field microscopy", Nature Methods, vol. 11, Issue 7, pp. 727-730, May 2014.

Quirin et al., "Calcium imaging of neural circuits with extended depth-of-field light-sheet microscopy," Optics Letters, vol. 41, No. 5, pp. 855-858, Mar. 2016.

Sikkel et al., "High speed sCMOS-based oblique plane microscopy applied to the study of calcium dynamics in cardiac myocytes", Journal of Biophotonics 9, No. 3, p. 311-323, Mar. 1, 2016.

Swoger et al., "Light-Sheet-Based Fluorescence Microscopy for Three-Dimensional Imaging of Biological Samples", Adapted from Imaging: A Laboratory Manual (ed. Yuste). CSHL Press, Cold Spring Harbor, NY, USA, Jan. 1, 2011, copyrighted 2014 (downloaded Jun. 5, 2016).

Tomer et al., SPED light sheet microscopy: fast mapping of biological system structure and function. Cell 163.7 (Nov. 2015): 1796-1806.

Truscott et al., "Determining 3D Flow Fields via Multi-camera Light Field Imaging", Journal of Visualized Experiments: Jove, Mar. 6, 2013, vol. 73, p. 4325.

* cited by examiner

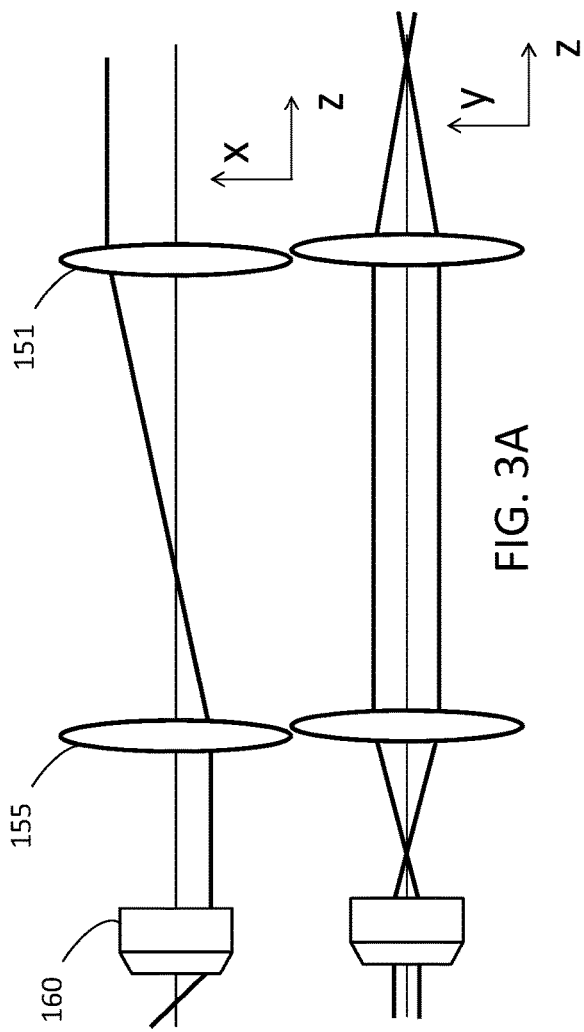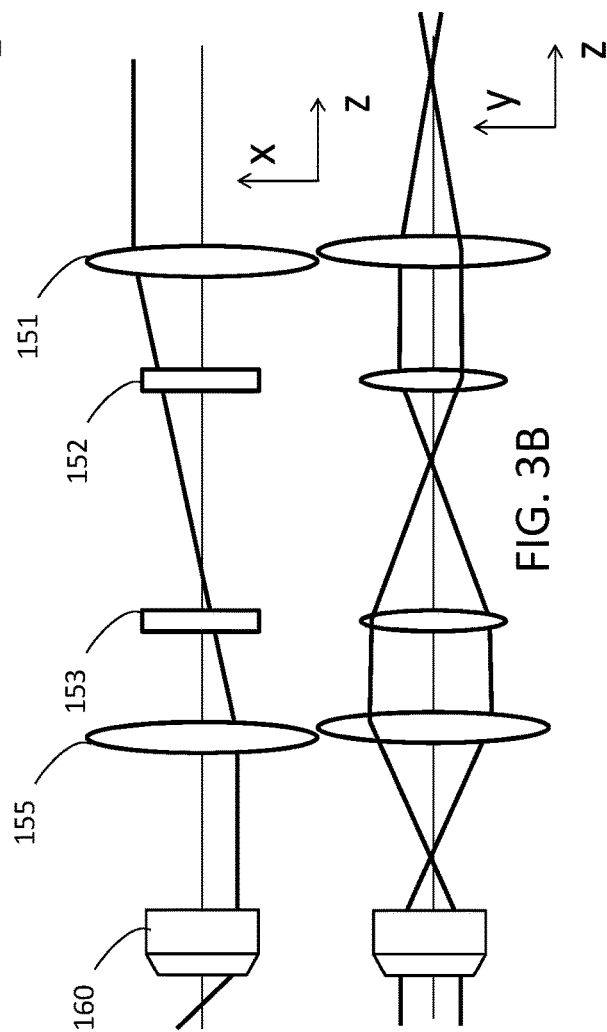

THREE-DIMENSIONAL IMAGING USING SWEPT CONFOCALLY ALIGNED PLANAR EXCITATION WITH ASYMMETRICAL MAGNIFICATION

CROSS REFERENCE TO RELATED APPLICATIONS

This Application is a U.S. national stage filing under 35 U.S.C. § 371 of International Application No. PCT/US2017/034945, filed May 30, 2017, which claims the benefit of U.S. Provisional Application No. 62/343,103, filed May 30, 2016, and U.S. Provisional Application No. 62/402,011, filed Sep. 30, 2016, each of which is incorporated herein by reference in its entirety.

STATEMENT REGARDING FEDERALLY-SPONSORED RESEARCH

This invention is made with government support under grants NS094296, NS076628, NS063226, and NS053684 awarded by the National Institutes of Health. The government has certain rights in the invention.

BACKGROUND

A variety of embodiments for implementing imaging using swept, confocally aligned planar excitation (SCAPE) are disclosed in publication WO 2015/109323, which is incorporated herein by reference in its entirety.

SUMMARY OF THE INVENTION

One aspect of the invention is directed to a first imaging apparatus. This apparatus comprises a first set of optical components having a proximal end and a distal end, and the first set of optical components includes an objective disposed at the distal end of the first set of optical components. This apparatus also comprises a second set of optical components having a proximal end and a distal end, and the second set of optical components includes an objective disposed at the distal end of the second set of optical components. The second set of optical components has a first magnification in a first radial direction and a second magnification in a second radial direction that is perpendicular to the first radial direction, and the first magnification is at least 1.5 times the second magnification. This apparatus also comprises a scanning element that is disposed proximally with respect to the proximal end of the first set of optical components and proximally with respect to the proximal end of the second set of optical components. The scanning element is arranged to route a sheet of excitation light so that the sheet of excitation light will pass through the first set of optical components in a proximal to distal direction and project into a sample that is positioned distally beyond the distal end of the first set of optical components, wherein the sheet of excitation light is projected into the sample at an oblique angle, and wherein the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane.

In some embodiments of the first apparatus, the detection light arriving from the sample has a depth dimension and a width dimension that is perpendicular to the depth dimension, and the magnification in the first radial direction in the second set of optical components corresponds to magnification of the width dimension of the detection light. In some of these embodiments, the light detector array comprises a 2D image sensor with pixels arranged in a plurality of readout rows, and the light detector array is oriented so that each of the plurality of readout rows corresponds to a respective different position in the depth direction of the detection light. The captured images of the intermediate image plane are arranged in frames, and each frame includes data from not more than half of the rows or not more than one quarter of the rows.

In some embodiments of the first apparatus, the light detector array comprises a 2D image sensor with pixels arranged in a plurality of readout rows, and the light detector array is oriented so that each of the plurality of readout rows corresponds to a respective different position in the depth direction of the detection light.

In some embodiments of the first apparatus, the detection light arriving from the sample has a depth dimension and a width dimension that is perpendicular to the depth dimension, the magnification in the first radial direction in the second set of optical components corresponds to magnification of the width dimension of the detection light, the first set of optical components has a uniform magnification in all radial directions, and the uniform magnification of the first set of optical components is the same as the second magnification of the second set of optical components. In some of these embodiments, the first magnification is at least 2 times the second magnification. In some of these embodiments, the first set of optical components comprises a first set of spherical optical components, and the second set of optical components comprises (a) a second set of spherical optical components with a magnification that matches the first set of spherical optical components and (b) a set of cylindrical optical components.

Some embodiments of the first apparatus further comprise a light sheet generator that expands light from a light source into the sheet of excitation light and a beam splitter disposed between the proximal end of the second set of optical components and the scanning element. The beam splitter is arranged to route the sheet of excitation light, which arrives from the light sheet generator, towards the scanning element; and the beam splitter is arranged to route the detection light, which arrives from the scanning element, into the proximal end of the second set of optical components. In some of these embodiments, the light sheet generator comprises a light source and at least one of (a) a cylindrical lens arranged to expand light from the light source into the sheet of excitation light; (b) an aspheric mirror arranged to expand light from the light source into the sheet of excitation light; (c) a spatial light modulator arranged to expand light from the light source into the sheet of excitation light; (d) a second scanning element arranged to expand light from the light source into the sheet of excitation light; and (e) an oscillating galvanometer mirror arranged to expand light from the light source into the sheet of excitation light.

Some embodiments of the first apparatus further comprise a light sheet generator that expands light from a light source into the sheet of excitation light, and the second set of optical components is arranged to route the sheet of excitation light, which arrives from the light sheet generator, in a distal to proximal direction towards the scanning element. In some of these embodiments, the light sheet generator comprises a light source and at least one of (a) a cylindrical lens arranged to expand light from the light source into the sheet of excitation light; (b) an aspheric mirror arranged to expand light from the light source into the sheet of excitation light; (c) a spatial light modulator arranged to expand light from the light source into the sheet of excitation light; (d) a second scanning element arranged to expand light from the light source into the sheet of excitation light; and (e) an oscillating galvanometer mirror arranged to expand light from the light source into the sheet of excitation light.

In some embodiments of the first apparatus, the light detector array comprises a 2D image sensor positioned at the intermediate image plane at an angle that matches a focal plane of the intermediate image.

In some embodiments of the first apparatus, the light detector array comprises a 2D image sensor positioned at a position that is remote from the intermediate image plane, and optical elements that route light from the intermediate image plane to the 2D image sensor.

In some embodiments of the first apparatus, the scanning element comprises a galvanometer mirror. In some embodiments of the first apparatus, the intermediate image plane is stationary.

Another aspect of the invention is directed to a first method of imaging a sample. This method comprises projecting a sheet of excitation light into a sample, wherein the sheet of excitation light is projected into the sample at an oblique angle, and wherein the sheet of excitation light is projected into the sample at a position that varies with time. This method also comprises routing detection light arriving from the sample into a proximal end of an optical system that has a first magnification in a first radial direction and a second magnification in a second radial direction that is perpendicular to the first radial direction, wherein the first magnification is at least 1.5 times the second magnification. This method also comprises forming a stationary intermediate image plane at a distal end of the optical system, and capturing images of the intermediate image plane at a plurality of times.

In some embodiments of the first method, the detection light arriving from the sample has a depth dimension and a width dimension that is perpendicular to the depth dimension, and the magnification in the first radial direction in the optical system corresponds to magnification of the width dimension of the detection light.

In some embodiments of the first method, the first magnification is at least 2 times the second magnification.

In some embodiments of the first method, the sheet of excitation light is projected into the sample at a position that varies with time depending on an orientation of a scanning element, the routing step is implemented by the scanning element, and each of the images of the intermediate image plane corresponds to a different orientation of the scanning element. In some of these embodiments, the detection light arriving from the sample has a depth dimension and a width dimension that is perpendicular to the depth dimension, and the magnification in the first radial direction in the optical system corresponds to magnification of the width dimension of the detection light.

Another aspect of the invention is directed to a second imaging apparatus. This apparatus comprises a first set of optical components having an objective, and the first set of optical components is arranged to (a) route excitation light into the objective so as to generate a sweeping sheet of excitation light through the objective and (b) simultaneously route image light returning through the objective along a detection path. This apparatus also comprises a second set of optical components disposed in the detection path arranged to receive light from the first set of optical components and produce an asymmetrically magnified oblique real image by magnifying in a first radial direction at a power of at least 1.5 times that in a second radial direction perpendicular to the first radial direction. This apparatus also comprises a light detector array positioned to sample the oblique real image.

In some embodiments of the second apparatus, the detection path includes a scanning element that routes the image light from the first set of optical components into the second set of optical components, and the scanning element also routes the sheet of excitation light into the first set of optical components. In some of these embodiments, the first set of optical components provides symmetric magnification between the objective and the scanning element.

In some embodiments of the second apparatus, the oblique real image has a first dimension whose pixels resolve light from multiple depths along an optical axis in front of the objective and a second dimension perpendicular the first dimension whose pixels resolve light from multiple positions along an axis transverse to the optical axis.

In some embodiments of the second apparatus, the light detector array comprises a 2D image sensor. Some of these embodiments further comprise a sampling controller that reads out the pixels of the light detector array row by row, wherein the rows correspond to the second dimension. In some of these embodiments, the sampling controller reads out only a fraction of the total number of rows of the light detector array for each of position of the scanning element.

In some embodiments of the second apparatus, the second set of optical components produce the asymmetrically magnified image by magnifying in the first radial direction at a power of at least 2 times that in the second radial direction.

In some embodiments of the second apparatus, the detection path and an excitation path both pass through a beam splitter. In some of these embodiments, the beam splitter is a dichroic beam splitter.

In some embodiments of the second apparatus, the second set of optical components includes a plurality of cylindrical lenses. In some embodiments of the second apparatus, the light detector array defines a plane forming an oblique angle with respect to an optical axis of the detection path.

Another aspect of the invention is directed to a third imaging apparatus. This apparatus comprises a light source, a cylindrical lens or a scanner that expands light from the light source into a sheet of light, a beam splitter disposed in a path of the sheet of light, a scanning element disposed in a path of the sheet of light, a first set of optical components having a proximal end and a distal end, with a first objective disposed at the distal end of the first set of optical components, and a second set of optical components having a proximal end and a distal end, with a second objective disposed at the distal end of the second set of optical components. The beam splitter routes the sheet of light towards the scanning element, and the scanning element routes the sheet of light into the proximal end of the first set of optical components. The first set of optical components routes the sheet of light in a proximal to distal direction through the first objective, accepts fluorescent light through the first objective, and routes the fluorescent light in a distal to proximal direction back to the scanning element. The scanning element routes the fluorescent light through the beam splitter and into the proximal end of the second set of optical components. The second set of optical components routes the fluorescent light in a proximal to distal direction through the second objective to form an intermediate image plane. This apparatus also comprises a light detector array optically positioned to capture images at the intermediate image plane.

In some embodiments of the third apparatus, the light detector array comprises a 2D image sensor positioned at the intermediate image plane at an angle that matches a focal plane of the intermediate image.

In some embodiments of the third apparatus, the light detector array comprises a 2D image sensor positioned at a position that is remote from the intermediate image plane and optical elements that route light from the intermediate image plane to the 2D image sensor.

In some embodiments of the third apparatus, a magnification of the first set of optical components matches a magnification of the second set of optical components.

In some embodiments of the third apparatus, the second set of optical components includes lenses having spherical components that magnify the image at the intermediate plane in all directions and cylindrical components that magnify the image at the intermediate plane in the Y direction only, and the magnification of the first set of optical components matches the magnification of the spherical components of the second set of optical components.

Some embodiments of the third apparatus further comprise a spatial light modulator disposed between the light source and the beam splitter.

In some embodiments of the third apparatus, the beam splitter reflects the light from the light source and transmits the fluorescent light. In some embodiments of the third apparatus, the intermediate image plane is stationary.

Another aspect of the invention is directed to a fourth imaging apparatus. This apparatus comprises a first set of optical components having a proximal end and a distal end, and the first set of optical components includes an objective disposed at the distal end of the first set of optical components. This apparatus also comprises a second set of optical components having a proximal end and a distal end, and the second set of optical components includes an objective disposed at the distal end of the second set of optical components. This apparatus also comprises a scanning element that is disposed proximally with respect to the proximal end of the first set of optical components and proximally with respect to the proximal end of the second set of optical components. This apparatus also comprises a light source; beam forming optics configured to shape the light from the light source into a sheet of excitation light; and a spatial light modulator configured to modify a characteristic of the sheet of excitation light. The scanning element is arranged to route the sheet of excitation light so that the sheet of excitation light will pass through the first set of optical components in a proximal to distal direction and project into a sample that is positioned distally beyond the distal end of the first set of optical components. The sheet of excitation light is projected into the sample at an oblique angle, and the sheet of excitation light is projected into the sample at a position that varies depending on an orientation of the scanning element. The first set of optical components routes detection light from the sample in a distal to proximal direction back to the scanning element. The scanning element is also arranged to route the detection light so that the detection light will pass through the second set of optical components in a proximal to distal direction and form an intermediate image plane at a position that is distally beyond the distal end of the second set of optical components. This apparatus also comprises a light detector array arranged to capture images of the intermediate image plane.

In some embodiments of the fourth apparatus, the spatial light modulator is configured to modify at least one of (a) a numerical aperture of the sheet of excitation light, (b) a tilt of the sheet of excitation light, and (c) a flatness of the sheet of excitation light. In some embodiments of the fourth apparatus, the spatial light modulator is configured so that the sheet of excitation light that is projected into the sample follows a Bessel beam function.

In some embodiments of the fourth apparatus, the light source comprises an incoherent light source. In some embodiments of the fourth apparatus, at least one characteristic of the spatial light modulator is adjusted to implement alignment of the apparatus.

In some embodiments of the fourth apparatus, at least one characteristic of the spatial light modulator is adjusted to implement alignment of the apparatus based on feedback on image quality obtained using the light detector array. In some embodiments of the fourth apparatus, at least one characteristic of the spatial light modulator is adjusted to correct for aberrations of the apparatus.

In some embodiments of the fourth apparatus, the light detector array sequentially captures a set of images of a sample between a first time and at a subsequent time, and at least one characteristic of the spatial light modulator is adjusted to change a characteristic of the sheet of excitation light between the first time and the subsequent time. In some of these embodiments the at least one characteristic of the spatial light modulator is adjusted to change a numerical aperture of the sheet of excitation light. In some of these embodiments the at least one characteristic of the spatial light modulator is adjusted to shift a waist of the sheet of excitation light. In some of these embodiments the at least one characteristic of the spatial light modulator is adjusted at a plurality of times between the first time and the subsequent time to implement structured illumination.

Some embodiments of the fourth apparatus further comprise a beam splitter disposed between the proximal end of the second set of optical components and the scanning element. The beam splitter is arranged to route the sheet of excitation light towards the scanning element, and the beam splitter is arranged to route the detection light into the proximal end of the second set of optical components. In some of these embodiments, the beam forming optics comprises at least one of a cylindrical lens, an aspheric mirror, a second spatial light modulator, a second scanning element, and an oscillating galvanometer mirror.

In some embodiments of the fourth apparatus, the second set of optical components is arranged to route the sheet of excitation light in a distal to proximal direction towards the scanning element. In some of these embodiments, the beam forming optics comprises at least one of a cylindrical lens, an aspheric mirror, a second spatial light modulator, a second scanning element, and an oscillating galvanometer mirror.

In some embodiments of the fourth apparatus, the intermediate image plane is stationary.

Another aspect of the invention is directed to a second method of imaging a sample. This method comprises modifying a characteristic of the sheet of excitation light using a spatial light modulator. This method also comprises projecting the sheet of excitation light into a sample, wherein the sheet of excitation light is projected into the sample at an oblique angle, and wherein the sheet of excitation light is projected into the sample at a position that varies depending on an orientation of a scanning element. This method also comprises routing detection light arriving from the sample back to the scanning element; using the scanning element to reroute the detection light into a proximal end of an optical system; forming a stationary intermediate image plane at a distal end of the optical system; and capturing images of the intermediate image plane at a plurality of times, each of the times corresponding to a different orientation of the scanning element.

In some embodiments of the second method, the spatial light modulator is configured to modify at least one of (a) a numerical aperture of the sheet of excitation light, (b) a tilt of the sheet of excitation light, and (c) a flatness of the sheet of excitation light.

In some embodiments of the second method, at least one characteristic of the spatial light modulator is adjusted to implement alignment. In some embodiments of the second method, at least one characteristic of the spatial light modulator is adjusted to implement alignment based on feedback on image quality obtained from the captured images. In some embodiments of the second method, at least one characteristic of the spatial light modulator is adjusted to correct for aberrations. In some embodiments of the second method, at least one characteristic of the spatial light modulator is adjusted at a plurality of times to implement structured illumination.

Another aspect of the invention is directed to a fifth imaging apparatus. This apparatus comprises a light source; beam forming optics configured to shape the light from the light source into a sheet of excitation light; and a spatial light modulator configured to modify a characteristic of the sheet of excitation light. This apparatus also comprises a first set of optical components having an objective, wherein the first set of optical components is arranged to (a) route the sheet of excitation light into the objective so as to generate a sweeping sheet of excitation light through the objective and (b) simultaneously route image light returning through the objective along a detection path. This apparatus also comprises a second set of optical components disposed in the detection path arranged to receive light from the first set of optical components, and a light detector array positioned to sample the oblique real image.

In some embodiments of the fifth apparatus, the detection path includes a scanning element that routes the image light from the first set of optical components into the second set of optical component, and the scanning element routes the sweeping sheet of excitation light into the first set of optical components.

In some embodiments of the fifth apparatus, the spatial light modulator is configured to modify at least one of (a) a numerical aperture of the sweeping sheet of excitation light, (b) a tilt of the sweeping sheet of excitation light, and (c) a flatness of the sweeping sheet of excitation light.

In some embodiments of the fifth apparatus, the spatial light modulator is configured so that the sweeping sheet of excitation light follows a Bessel beam function.

In some embodiments of the fifth apparatus, the light source comprises an incoherent light source.

In some embodiments of the fifth apparatus, at least one characteristic of the spatial light modulator is adjusted to implement alignment of the apparatus. In some embodiments of the fifth apparatus, at least one characteristic of the spatial light modulator is adjusted to implement alignment of the apparatus based on feedback on image quality obtained using the light detector array. In some embodiments of the fifth apparatus, at least one characteristic of the spatial light modulator is adjusted to correct for aberrations of the apparatus.

In some embodiments of the fifth apparatus, the light detector array sequentially captures a set of images of a sample between a first time and at a subsequent time, and at least one characteristic of the spatial light modulator is adjusted to change a characteristic of the sheet of excitation light between the first time and the subsequent time. In some of these embodiments, the at least one characteristic of the spatial light modulator is adjusted to change a numerical aperture of the sheet of excitation light. In some of these embodiments, the at least one characteristic of the spatial light modulator is adjusted to shift a waist of the sheet of excitation light. In some of these embodiments, the at least one characteristic of the spatial light modulator is adjusted at a plurality of times between the first time and the subsequent time to implement structured illumination.

In some embodiments of the fifth apparatus, the beam forming optics comprises at least one of a cylindrical lens, an aspheric mirror, a second spatial light modulator, a second scanning element, and an oscillating galvanometer mirror.

Another aspect of the invention is directed to a sixth apparatus for imaging an eye of a live subject. This apparatus comprises a second set of optical components having a second proximal end and a second distal end; a second lens disposed distally beyond the second distal end; a first set of optical components having a first proximal end and a first distal end, wherein the first distal end is configured for positioning adjacent to the eye; and a scanning element that is disposed proximally with respect to the proximal end of the first set of optical components and proximally with respect to the proximal end of the second set of optical components. The scanning element is arranged to route excitation light through the first set of optical components in a proximal to distal direction and through the lens of the eye so as to project a sheet of excitation light into the retina at an oblique angle. A position of the sheet of excitation light within the retina varies depending on an orientation of the scanning element. The first set of optical components routes detection light from the retina in a distal to proximal direction back to the scanning element. The scanning element is also arranged to route the detection light so that the detection light will pass through the second set of optical components in a proximal to distal direction and form an intermediate image plane at a position that is distally beyond the second lens. This apparatus also comprises a light detector array arranged to capture images of the intermediate image plane.

In some embodiments of the sixth apparatus, the first distal end is configured for positioning adjacent to the eye at a position at which a distance between the first distal and the lens of the eye matches a distance between the second lens and the second distal end. In some of these embodiments, the first set of optical components has a magnification that matches the second set of optical components.

In some embodiments of the sixth apparatus, the first set of optical components has a magnification that matches the second set of optical components.

Some embodiments of the sixth apparatus further comprise a light source and a beam splitter disposed between the proximal end of the second set of optical components and the scanning element. The beam splitter is arranged to route the excitation light, which originates from the light source, towards the scanning element. The beam splitter is arranged to route the detection light, which arrives from the scanning element, into the proximal end of the second set of optical components. Some of these embodiments further comprise at least one of (a) a cylindrical lens arranged to expand light from the light source into a sheet; (b) an aspheric mirror arranged to expand light from the light source into a sheet; (c) a spatial light modulator arranged to expand light from the light source into a sheet; (d) a second scanning element arranged to expand light from the light source into a sheet; and (e) an oscillating galvanometer mirror arranged to expand light from the light source into a sheet.

Some embodiments of the sixth apparatus further comprise a light source, and the second set of optical components is arranged to route the excitation light, which originates from the light source, in a distal to proximal direction towards the scanning element. Some of these embodiments further comprise at least one of (a) a cylindrical lens arranged to expand light from the light source into a sheet; (b) an aspheric mirror arranged to expand light from the light source into a sheet; (c) a spatial light modulator arranged to expand light from the light source into a sheet; (d) a second scanning element arranged to expand light from the light source into a sheet; and (e) an oscillating galvanometer mirror arranged to expand light from the light source into a sheet.

In some embodiments of the sixth apparatus, the light detector array comprises a 2D image sensor positioned at the intermediate image plane at an angle that matches a focal plane of the intermediate image.

In some embodiments of the sixth apparatus, the light detector array comprises a 2D image sensor positioned at a position that is remote from the intermediate image plane, and optical elements that route light from the intermediate image plane to the 2D image sensor.

In some embodiments of the sixth apparatus, the intermediate image plane is stationary.

Another aspect of the invention is directed to a third method of imaging an eye of a live subject. This method comprises positioning a first set of optical components having a first proximal end and a first distal end so that the first distal end is adjacent to the eye; and routing excitation light through the first set of optical components so that the excitation light will pass through the first set of optical components in a proximal to distal direction and through the lens of the eye, and so that a sheet of excitation light is projected into the retina at an oblique angle, wherein a position of the sheet of excitation light within the retina varies depending on an orientation of a scanning element. This method also comprises routing detection light from the retina through the first set of optical components in a distal to proximal direction back to the scanning element; routing the detection light so that the detection light will pass through a second set of optical components in a proximal to distal direction and through a second lens disposed distally beyond the second set of optical components, and form an intermediate image plane at a position that is distally beyond the second lens; and capturing images of the intermediate image plane.

In some embodiments of the third method, the first set of optical components has a magnification that matches the second set of optical components. In some embodiments of the third method, the second lens has a magnification that matches the lens of the eye.

In some embodiments of the third method, the second set of optical components has a second distal end, and the positioning step comprises positioning the first distal end at a position at which a distance between the first distal end and the lens of the eye matches a distance between the second lens and the second distal end.

In some embodiments of the third method, the first set of optical components has a magnification that matches the second set of optical components, the second lens has a magnification that matches the lens of the eye, the second set of optical components has a second distal end, and the positioning step comprises positioning the first distal end at a position at which a distance between the first distal end and the lens of the eye matches a distance between the second lens and the second distal end.

In some embodiments of the third method, the intermediate image plane is stationary.

BRIEF DESCRIPTION OF THE DRAWINGS

FIG. 3A shows details of the magnification in the X and Y directions in the FIG. 1 embodiment.

FIG. 3B shows details of the magnification in the X and Y directions in the FIG. 2A embodiment.

DESCRIPTION OF THE PREFERRED EMBODIMENTS

This application describes additional embodiments for implementing SCAPE-based imaging.

Section 1: Asymmetric Magnification at the Detection Arm

Figure 1:
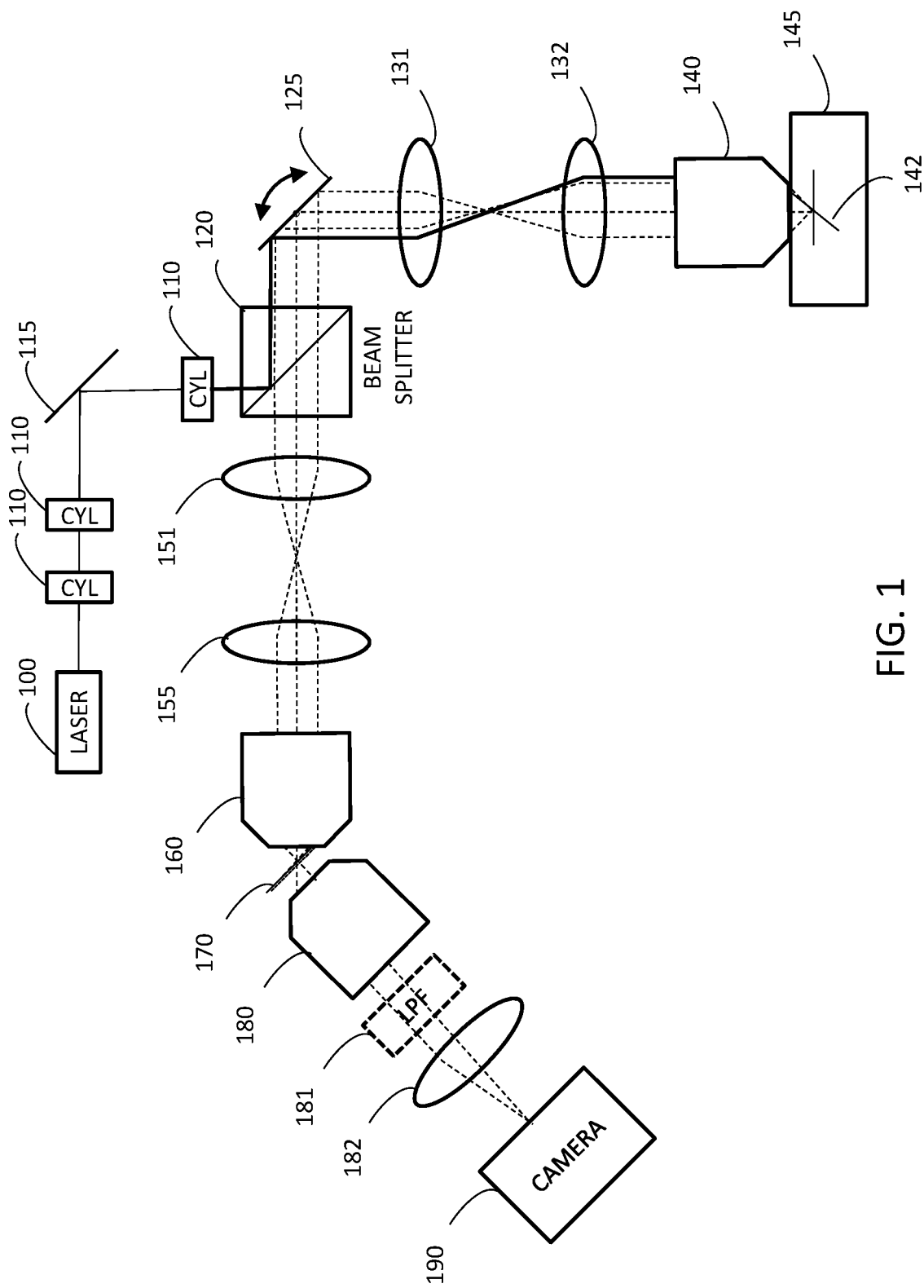
FIG. 1 depicts an embodiment of a SCAPE system that uses a magnifier to expand the image and route the image to a light detector array.

FIG. 1 is a first embodiment of a SCAPE system. Light from the light source (e.g., laser 100 or an LED) is routed towards a dichroic beam splitter 120 by one or more routing mirrors 115, and expanded from a pencil beam into a sheet by one or more cylindrical lenses 110. The sheet of light is reflected by the beam splitter 120 towards a scanning element 125. In some embodiments, this scanning element 125 comprises an oscillating galvanometer mirror. In alternative embodiments, the scanning element 125 could be implemented using an oscillating prism or any of a variety of alternative designs that will be apparent to persons skilled in the relevant arts.

After being rerouted by the scanning element 125, the sheet of light continues down the excitation arm in a proximal to distal direction through a first set of optical components (e.g., lenses 131, 132 and objective 140). The sheet of light then enters the sample at an oblique angle and penetrates the sample along the Z direction, resulting in a sheet of light 142 within the sample 145. When the scanning element moves (e.g., due to oscillation of the galvanometer mirror), it causes the position of the sheet of light 142 within the sample 145 to change. Thus, the position of the sheet of excitation light within the sample varies depending on the orientation of the scanning element 125.

The excitation light excites fluorescence in the sample 145, and the fluorescence is imaged. The path of the fluorescent light from the sample 145 to the detector first passes through the first set of optical components 131-140 in a distal to proximal direction and back to the scanning element 125. From there, the fluorescent light passes through the dichroic beam splitter 120 and into the detection arm. The detection arm includes a second set of optical components (e.g., lenses 151, 155 and second objective 160). The fluorescent light passes through these components 151-160 in a proximal to distal direction and forms an intermediate image plane 170. Because the sheet of light entered the sample 145 at an oblique angle, the intermediate image plane 170 will be tilted with respect to the optical axis of lenses 151, 155.

In this embodiment, the first set of optical components is arranged to (a) route excitation light into the objective so as to generate a sweeping sheet of excitation light through the objective and (b) simultaneously route image light returning through the objective along a detection path. The second set of optical components is disposed in the detection path and is arranged to receive light from the first set of optical components and produce an asymmetrically magnified oblique real image by magnifying in a first radial direction at a power of at least 1.5 times that in a second radial direction perpendicular to the first radial direction. A light detector array is positioned to sample the oblique real image. Optionally, the detection path includes a scanning element that routes the image light from the first set of optical components into the second set of optical components, and the scanning element also routes the sheet of excitation light into the first set of optical components. One of the advantages of this configuration of SCAPE is that the position of the intermediate image plane 170 remains stationary, regardless of changes in the position of the sheet of light 142 within the sample 145.

In alternative embodiments, instead of using the cylindrical lenses 110 to convert the pencil-shaped beam from the light source (e.g., laser 100) into a fan-shaped sheet, one of the routing mirrors 115 may be replaced by a second scanning mirror oriented to scan the pencil shaped beam so as to create a virtual sheet of light. Note that as used herein, the term "sheet of light" includes these virtual sheets of light as well as true sheets of light (e.g., light sheets formed using one or more cylindrical lenses).

In order to capture the image that appears at the tilted intermediate image plane 170, a variety of approaches may be used. In the FIG. 1 embodiment, a magnifier is used to expand the image and route the image to a light detector array (e.g., camera 190). This magnifier includes a third objective 180 and additional optical components (e.g., lens 182 and optional long pass filter 181). The light detector array (e.g., camera 190) captures images of the tilted intermediate image plane 170.

In some embodiments, the first set of optical components 131-140 in the excitation arm matches the second set of optical components 151-160 in the detection arm. The same scanning element 125 is used in both the excitation path and the detection path. This configuration is advantageous because it cancels out certain optical distortions that are very difficult to cancel using alternative approaches. For example, if the magnification of the second set of optical components 151-160 in the detection arm is higher than the magnification of the first set of optical components 131-140 in the excitation arm, the image that appears at the tilted intermediate image plane 170 will be distorted.

When the optical components in the excitation arm matches the optical components in the detection arm, the scale of the tilted intermediate image plane 170 will match the scale of the sheet of light 142 that extends into the sample 145. For example, 1 micron in the Z direction at the sample 145 (i.e., the depth direction, which is the direction at which the excitation light propagates within the sample 145) will correspond to 1 micron at the tilted intermediate image plane 170. And 1 micron in the Y direction at the sample 145 (i.e., the width direction, which is the direction that is perpendicular to the page in FIG. 1) will correspond to 1 micron at the tilted intermediate image plane 170 in the direction that is perpendicular to the page of FIG. 1.

When capturing light, cameras that have larger pixels are often used because larger pixels capture more light than smaller pixels. For example, many conventional cameras have pixels that measure 7 µm×7 µm. If we want to achieve resolution of 1.4 µm at the sample 145, and a camera that has 7 µm pixels is used, we must magnify the image by a factor of 5 to expand the 1.4 µm pixels at the tilted intermediate image plane 170 to match the 7 µm pixels in the camera 190. This can be accomplished by the magnifier that includes the third objective 180 and the additional optical components 181, 182. (Note that resolution at the sample in the X direction can be selected by the system designer and is controlled by scanning because when the scanning element 125 moves, the sheet of light 142 will move within the sample 145 by a corresponding amount.) By placing the magnifier 180-182 in front of the camera 190, we obtain 1.4 µm resolution at the sample 145, and each of those 1.4 µm pixels maps onto a corresponding 7 µm pixel at the camera 190.

The FIG. 1 embodiment has a number of advantages. It relies on a single galvanometer scanner 125 and a dichroic beam splitter 120. (In alternative embodiments, a rotating polygon may be used in place of these components.) The orthogonal alignment of the excitation arm and the detection arm makes this embodiment easier to assemble and align. Distortion is avoided because the optical components in the excitation arm match the optical components in the detection, as explained above. The configuration is also analogous to the standard layout for confocal imaging. This makes it possible to implement a dual-mode confocal/SCAPE system by making minor modifications to the configuration depicted in FIG. 1. These modifications include, for example, adjusting the position of the routing mirrors 115 along the X axis, and adding a 45° mirror above the first objective 140 to permit switching between the upright and inverted configurations.

The FIG. 1 embodiment however, has a significant disadvantage. Because the intermediate image plane 170 is tilted with respect to the optical axis of lenses 151, 155, the camera 190 and magnifier 180-182 in front of the camera 190 are mounted to match the angle of the tilt of the intermediate image plane 170. As a result, a large portion of the light traveling to the left after it passes through the second objective 160 in the detection arm will not be captured by the camera 190. This lost light corresponds to lost signal and a corresponding decrease in signal-to-noise ratio.

One possible approach for overcoming the above-identified problem (i.e., that a large portion of light is lost in the FIG. 1 embodiment) would be to position the 2D camera sensor at the position of the tilted intermediate image plane 170. In that configuration, the light traveling to the left out of the second objective 160 would fall directly on the 2D camera sensor, in which case most of that light would be captured. But this configuration has a different problem. Because conventional high-sensitivity camera sensors have large pixels (e.g., 7 µm), and because the image at the tilted intermediate image plane is the same size as the sheet of light 142 in the sample 145, this would mean that the best resolution that can be obtained at the sample would be 7 µm resolution in both the Y direction and the Z direction. And 7 µm resolution may not be sufficient to resolve the structures of interest in the sample 145. One might think that this deficiency could be surmounted by increasing the magnification of the second set of optical components in the detection arm. But increasing the magnification in the detection arm introduces distortion, and also increases the steepness of the tilt angle of the intermediate image plane 170, which causes a variety of other problems.

Another possible approach for overcoming the above identified problems would be to place a camera sensor with smaller pixels (e.g. on a 1.4 µm pitch) at the tilted intermediate image plane 170. While this approach can provide usable images, the sensitivity of the device is drastically reduced. This is because the area of 7 µm×7 µm camera pixels is 25 times larger than the area of camera pixels that measure 1.4 µm×1.4 µm. And this 25× reduction in area reduces the sensitivity of the device.

Figure 2A:
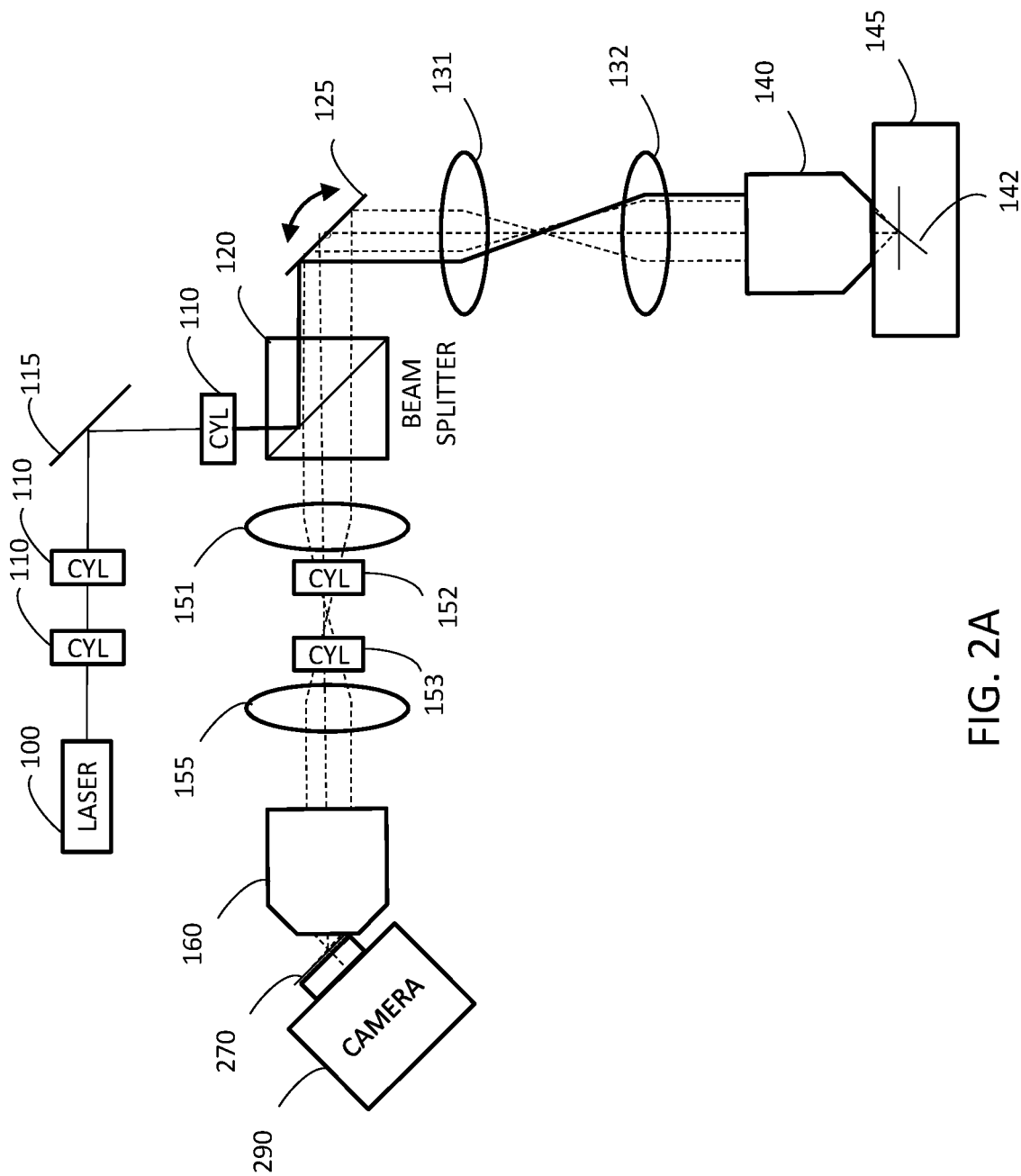
FIG. 2A depicts an embodiment of a SCAPE system that uses asymmetric magnification in the detection path with a first camera configuration.

The FIG. 2A embodiment uses asymmetric magnification in the detection path to provide a solution to these problems. More specifically, in the FIG. 2A embodiment, the second set of optical components has a first magnification in a first radial direction and a second magnification in a second radial direction that is perpendicular to the first radial direction, and the first magnification is at least 1.5 times the second magnification. In some embodiments, it is at least 2 times the second magnification. This may be accomplished (as it is in the FIG. 2A embodiment) by incorporating cylindrical optical components 152, 153 within the second set of optical components 151-160 in the detection arm. (Note that the FIG. 2A embodiment is similar to the FIG. 1 embodiment, except that cylindrical optical components are added to the detection arm in FIG. 2A.)

In the FIG. 2A embodiment, this asymmetric magnification is implemented using cylindrical lenses 152, 153 to increase the magnification of the image at the tilted intermediate image plane 270 in the Y direction only (i.e. the width direction that is perpendicular to the page). In these embodiments, the magnification in the first radial direction in the second set of optical components corresponds to magnification of the width dimension of the detection light. Notably, increasing magnification in the Y direction does not introduce the distortions discussed above. The camera 290 can then be positioned so that its image sensor is located at the tilted intermediate image plane 270, which avoids the losses associated with the off-axis third objective 180 in the FIG. 1 embodiment.

In some embodiments, the second set of optical components has both isotropic components (e.g., spherical lenses 151, 155) that magnify the image at the tilted intermediate plane in all radial directions and cylindrical components 152, 153 that magnify the image at the tilted intermediate plane in the radial direction that corresponds to the Y direction only. The isotropic magnification of the first set of optical components 131-140 preferably matches the isotropic magnification of the second set of optical components 151-160, but the optical characteristics in the direction that is perpendicular to the page will not match due to the cylindrical lenses 152, 153 that appear in the second set of optical components only.

In these embodiments, any magnification that occurs in the first set of optical components 131-140 is preferably symmetric and uniform in all radial directions. This uniform magnification is preferably the same as the magnification in the X direction that occurs in the second set of optical components 151-160.

When asymmetric (e.g., unilateral) magnification is used, rectangular pixels of the light sheet 142 in the sample 145 map onto square pixels in the camera 290. For example, in a system where the camera has 7 µm pixels, and the cylindrical lenses 152, 153 provide 5× magnification in the Y direction, rectangular regions that measure 1.4 µm×7 µm at the light sheet 142 in the sample 145 will map onto camera pixels that measure 7 µm×7 µm. In this example, we obtain 1.4 µm resolution in the Y direction at the sheet of light 142 in the sample 145; and we obtain 7 µm resolution in the Z direction at the sheet of light 142. (The resolution in the X direction can be set to any desired value by adjusting scanning because scanning shifts the position of the light sheet 142 within the sample 145.) Even though the resolution is only 7 µm resolution in the depth Z direction at the sample, this technique provides far better multiplane imaging than competing techniques. In addition, this approach maintains sensitivity because cameras with large pixels are used. This configuration advantageously captures almost all of the detected light, corresponding to a higher NA detection. It provides better resolution, higher throughput, and improved signal-to-noise. In addition, alignment requires only positioning of the camera, and there is no need it to align any of the additional optical components (e.g. components 180-182 that appear in the FIG. 1 embodiment but are not included in the FIG. 2A embodiment).

In another example, in a system where the camera has 7 µm pixels and the cylindrical optical components provide 2.5× magnification in the Y direction, rectangular regions that measure 2.8 µm×7 µm at the light sheet 142 in the sample 145 will map onto camera pixels that measure 7 µm×7 µm. Other magnification values for the Y direction (e.g. between 2× and 8×) may be used in alternative embodiments.

Because the resolution is different in the Z direction than the Y direction in these embodiments, we can take advantage of this difference to increase the read-out rate from the camera sensor. For example, in the FIG. 1 embodiment, if you want 1000 micron range along Y at the sample and 300 micron depth range Z, and you want a total of 500 pixels along the Y direction (i.e., 2 μm resolution), you will need to use 150 pixels along Z because the pixels are square. This corresponds to 150 rows at the camera. Because the readout speed in many commercially available cameras depends on the number of rows and not the number of columns, that 150 pixels in the Z direction dictates the camera's read-out rate.

In contrast, in the FIG. 2A embodiment, we scale the magnification of each dimension independently and decrease the number of pixels in the Z direction due to the lower resolution in that direction. As a result, each frame has fewer rows in the Z direction. For example, when 2× magnification is used, we only need to acquire 75 rows in the Z direction. This means that the FIG. 2A embodiment can capture frames at twice the speed of the FIG. 1 configuration, but still cover the same 300 micron depth without sacrificing resolution in the Y direction (or the X direction, which is governed by scanning) In some of these embodiments, each frame of image data includes data from not more than half of the rows of the image sensor, or from not more than one quarter of the rows of the image sensor.

In some embodiments, the ability to implement asymmetric magnification can be used to trade off lateral and depth resolution—e.g. to have good pixel resolution along y and x while reducing the number of rows used in z. This asymmetric magnification could permit faster speed acquisition at higher x-y resolutions with lower resolution in z (or vice versa). This additional degree of freedom would also allow adjustment of magnification within the primary telescopes 131, 132 and 151, 155 without changing the angle of the intermediate image plane, and thus the camera angle.

In some embodiments, a similar approach may be used to trade off resolution in a given direction. For example, the system may be switched to a lower resolution in order to achieve a higher frame rate. Conversely, the system may be switched to a lower frame rate in order to a cheese a higher resolution.

Optionally, these embodiments may be configured to take advantage of the fact that the camera read out is fastest at the center of the camera chip for particular cameras (e.g. the Andor Zyla camera). In these embodiments, it is preferable to re-position the image on the camera for samples where the range of depths to be imaged is different. For example, to obtain 300 rows in a thick sample, the sample can be maintained at the narrowest part of the light sheet, in which case the image can be positioned from the middle −150 to the middle +150 position on the camera chip. In another example, where a 50 row acquisition is being implemented, the image should be positioned in the middle −25 to middle+ 25 portion of the camera chip. In this latter situation, the image is translated up 125 rows on the camera). This translation may be implemented, for example, using steering mirrors on the detection arm, which can optionally be incorporated into an image splitter.

Note that in the FIG. 2A embodiment, asymmetric magnification is implemented using cylindrical lenses 152, 153 to increase the magnification of the image at the tilted intermediate image plane 270 in the Y direction only (i.e. the direction that is perpendicular to the page). But in alternative embodiments, the asymmetric magnification may be implemented in different directions. For example, asymmetric magnification may be used to increase the magnification of the image in the Z direction, but leave the image non-magnified in other directions. Optionally, the orientation of the image sensor/camera in these embodiments may be rotated 90 degrees so that the direction having decreased resolution aligns with the rows of the image sensor. This means that fewer rows can be read out for each frame, which can be relied on to increase the frame rate of the system as discussed above.

In some alternative embodiments, instead of using cylindrical lenses 152, 153 to provide the asymmetric magnification, alternative optical components (e.g. an SLM and/or aspheric mirrors) may be used to increase the magnification of the image at the tilted intermediate image plane 270 in the desired direction.

In a variation of the FIG. 2A approach, cylindrical optical components are included in the detection arm in order to implement asymmetric magnification, and a sensor that has small pixels (e.g. 1.4 μm by 1.4 μm) is placed at the tilted intermediate image plane 270. The magnification provided by the cylindrical optical components will magnify a square region that measures 1.4 μm on each side onto a plurality of pixels at the sensor. For example, when 5× magnification is used, a square 1.4 μm region on the light sheet 142 in the sample 145 will be projected onto five adjacent pixels on the camera 290 (which together occupy a region that measures 1.4 μm×7 μm). The data in these five adjacent pixels can then be binned together. This technique may be used to trade off resolution between the Z and Y directions and/or trading off sensitivity with resolution. Note that when this technique is used, the total number of pixels in the camera 290 is increased. If the pixel count exceeds the pixel count of commercially available sensors, multiple sensors may be mounted at the tilted intermediate image plane 270 in a tiled configuration.

Figure 2B:
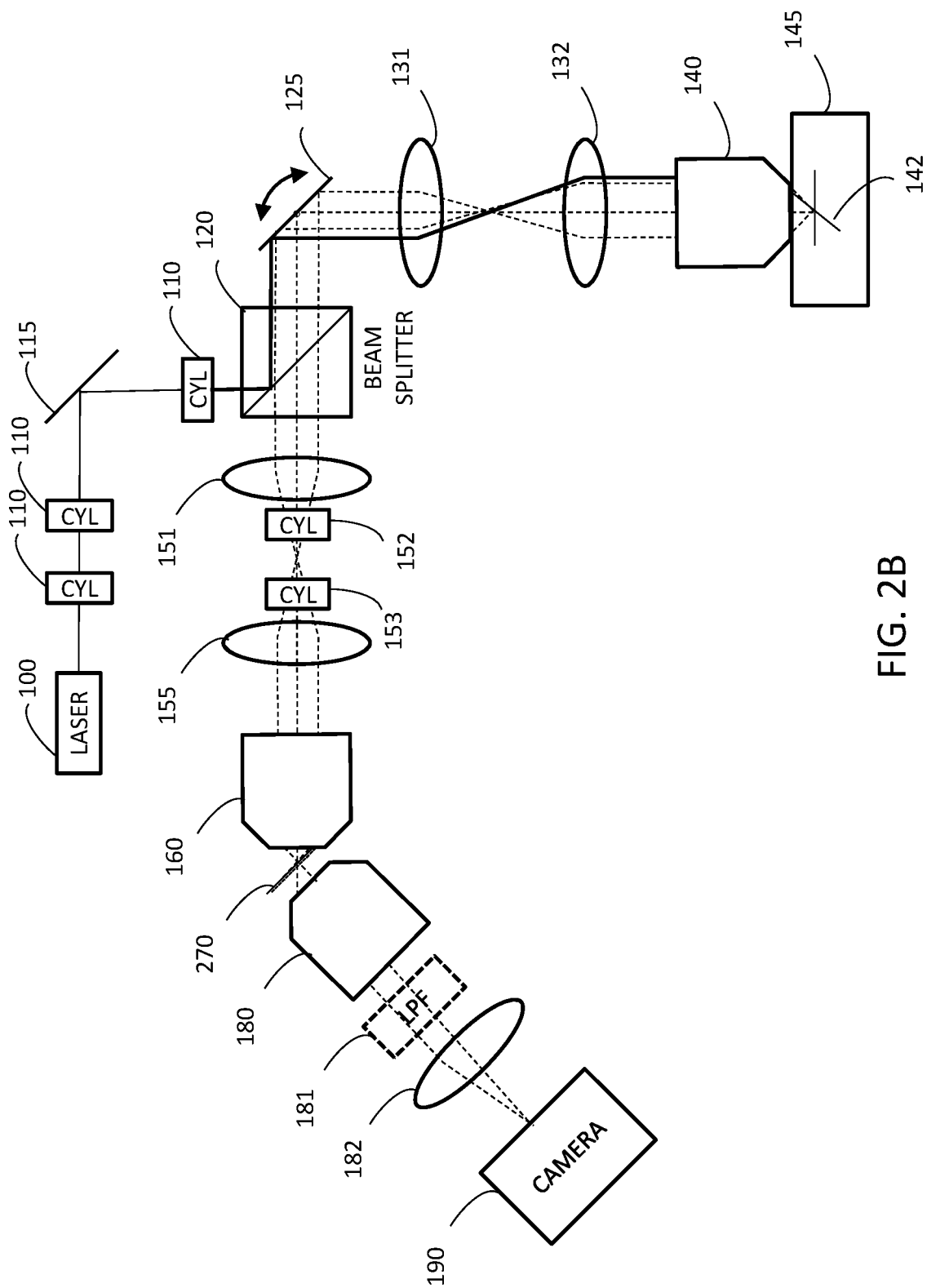
FIG. 2B depicts an embodiment of a SCAPE system that uses asymmetric magnification in the detection path with an alternative camera configuration.

FIG. 2B is similar to the FIG. 2A embodiment, except that the camera 290 of the FIG. 2A embodiment is replaced with the same third objective 180, additional components 181, 182, and the camera 190 that were used in the FIG. 1 embodiment. Those components 180-190 in the FIG. 2B embodiment work the same way as the corresponding components in the FIG. 1 embodiment. Although a significant amount of light is lost before it reaches the camera 190 in the FIG. 2B embodiment, it remains a viable option.

Figure 2C:
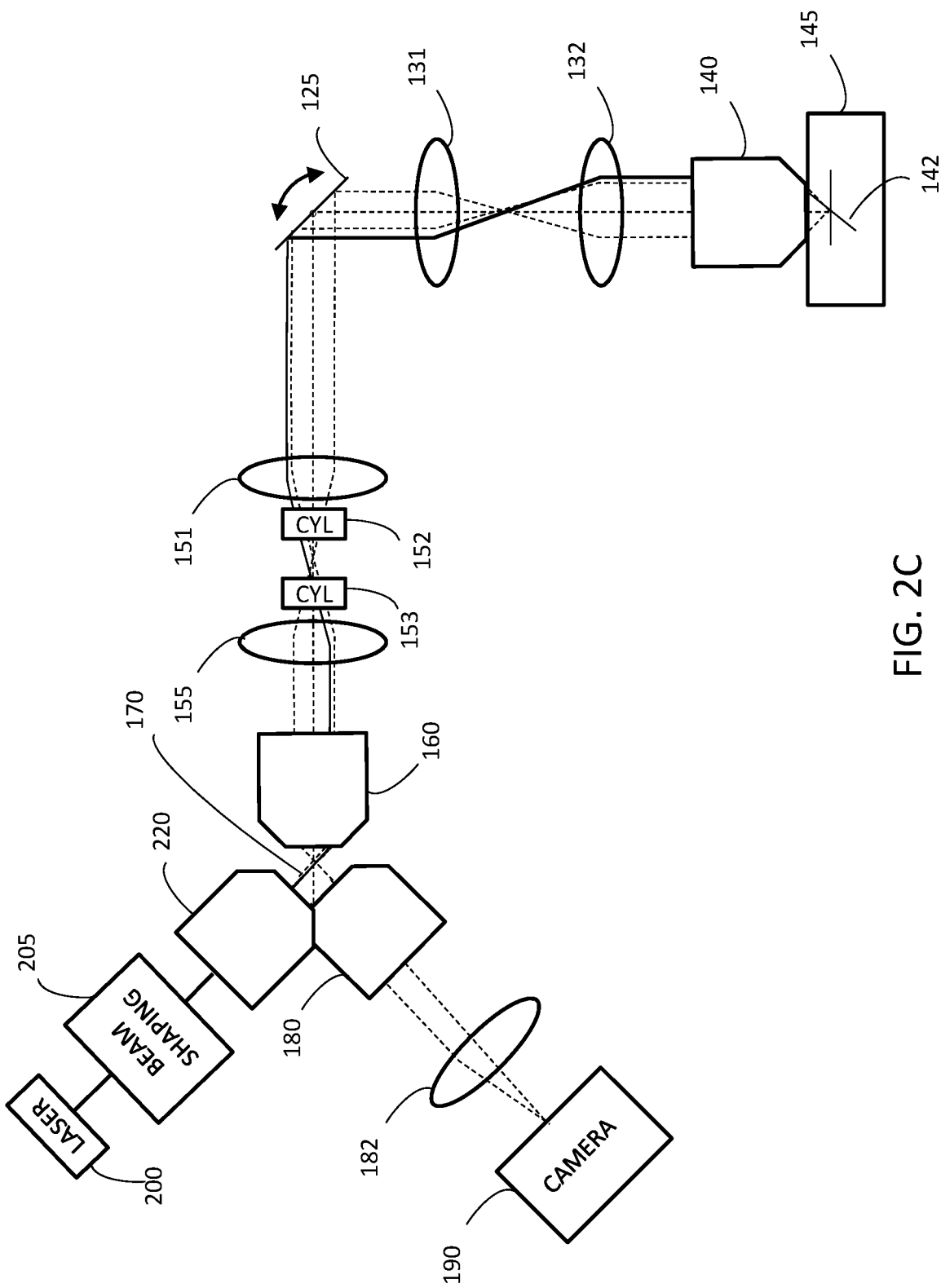
FIG. 2C depicts an embodiment of a SCAPE system that uses asymmetric magnification in the detection path with an alternative configuration for introducing the sheet of excitation light.

FIG. 2C is similar to the FIG. 2B embodiment, except that instead of introducing the sheet of excitation light into the system via the beam splitter 120 of FIG. 2B (which is disposed between the proximal end of the second set of optical components 151-160 and the scanning element 125), that beam splitter is omitted, and the sheet of excitation light is introduced into the system by injecting the sheet via the second objective 160 so that it passes in a distal to proximal direction through the second set of optical components 151-160. In this FIG. 2C embodiment, a light source 200 (e.g. a laser or an LED) generates a pencil-shaped beam of light, and beam shaping optics 205 expands that pencil-shaped beam into a sheet of excitation light. This sheet of excitation light is then introduced to the fourth objective 220. The sheet of excitation light passes through the fourth objective 220 and enters the distal end of the second set of optical components 151-160. The sheet of excitation light then passes through the second set of optical components 151-160 in a distal to proximal direction until it reaches the scanning element 125. Subsequently, operation of the FIG. 2C embodiment resembles that of the FIG. 2B embodiment.

Note that in the FIG. 2C embodiment, the sheet of excitation light passes in a distal to proximal direction through the second set of components 151-160. Because those components include cylindrical lenses 152, 153, they will reduce the width of the sheet of excitation light. In these embodiments, it is preferable to inject an extra-wide sheet of excitation light into the objective 160 so that it retains a usable width even after that its width has been reduced.

FIGS. 3A and 3B show how the cylindrical lenses 152, 153 (which appear in each of the FIGS. 2A, 2B, and 2C embodiments) change the magnification in the Y direction but does not change the magnification in the X direction. More specifically, FIG. 3A shows what the magnification would be in both the X and Y directions (top and bottom respectively) with the ordinary set of optical components 151, 155 used in the FIG. 1 embodiment. And FIG. 3B shows what the magnification would be in both the X and Y directions (top and bottom respectively) when the cylindrical lenses 152, 153 that are used in the detection arm of the FIG. 2A/2B/2C embodiments are added. As can be seen by comparing the left sides of FIGS. 3A and 3B, the magnification increases in the Y direction only when the cylindrical lenses 152, 153 are included.

Section 2: Optimizing the Point Spread Function of the Excitation Side

Figure 4:
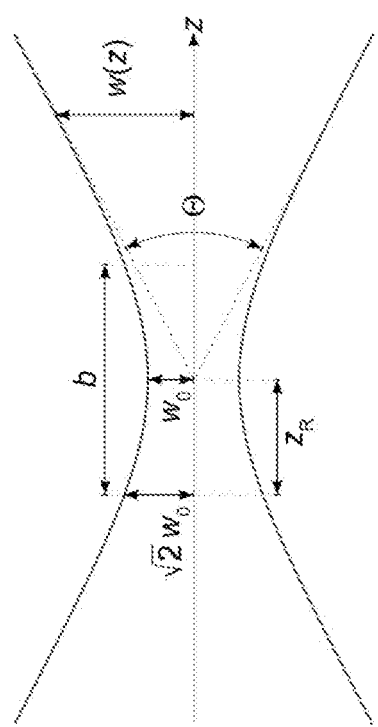
FIG. 4 depicts the cross-section of a Gaussian light sheet that is projected into the sample in the FIG. 1 embodiment.

One of the major limitations on resolution in SCAPE systems is the thickness of the light sheet illumination. (This is also a problem for conventional light sheet microscopy.) Many SCAPE systems use a simple Gaussian beam, and the cross-section of these Gaussian beams is illustrated in FIG. 4. One characteristic of the Gaussian beam is that its axial thickness pattern is governed by the numerical aperture (NA) of the sheet (from the width of the beam entering the objective). As a result, the wider the NA (corresponding to a large Θ), the narrower the sheet at the focal plane (corresponding to a small $w_0$), but the faster the broadening of the sheet from that central point onwards. (I.e., b will be small, which corresponds to a low depth of field). For a lower NA, $w_0$ is bigger (less resolution) but b is bigger (longer depth of field). In the case of conventional light sheet imaging, this condition limits the lateral field of view. And in SCAPE systems, this can limit the useful depth of field. Overcoming this condition can result in higher resolution over a larger range of depths. (Note that scattering also contributes to limiting this dimension.)

Spatial light modulators (SLMs) e.g., digital mirror devices, phase/amplitude LCDs can generate almost arbitrary 3D illumination patterns. In some embodiments, one of these SLMs may be used to shape, craft and optimize the light sheet entering the sample to be optimized to flatten the light sheet at the relevant depths.

Figure 5A:
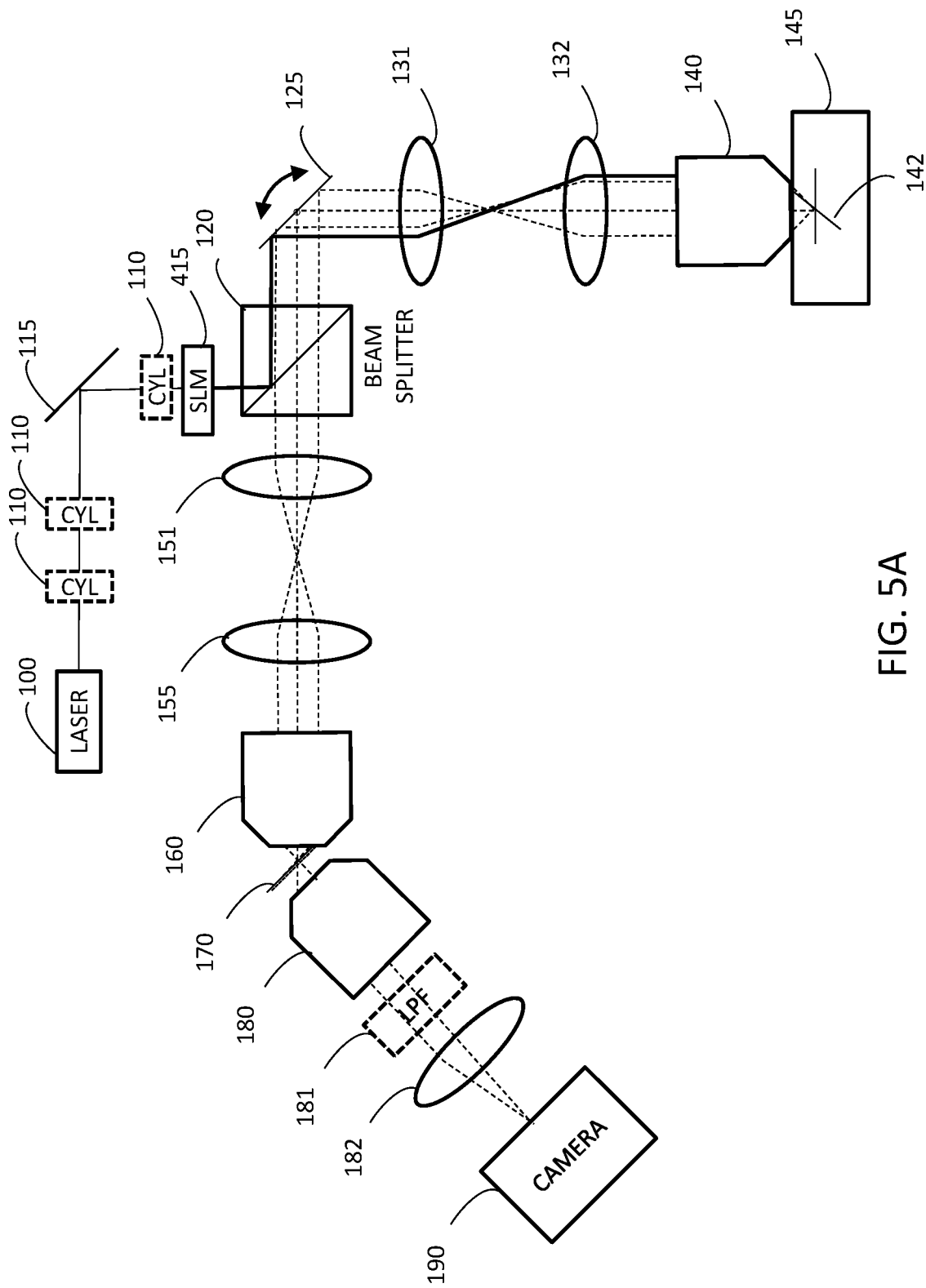
FIG. 5A is a block diagram of a system that incorporates an SLM to optimize the light sheet.

FIG. 5A is a block diagram of an embodiment that incorporates an SLM to optimize the light sheet for use a particular context. The operation of the FIG. 5A embodiment is similar to the operation of the FIG. 1 embodiment, except that the FIG. 5A embodiment includes a spatial light modulator 415 that is used to expand the light from the light source 100 into a sheet. Optionally, additional beam preconditioning/expansion components (e.g., cylindrical lenses 110) may be included prior to the SLM 415. Optionally, an LED or other incoherent light source may be used as the light source in place of the laser 100, particularly in connection with the FIG. 5A/5B embodiments. The use of LEDs may be advantageous for minimizing speckle.

Note that in alternative embodiments, the components 180-182 that sit between the tilted intermediate image plane and the camera 190 may be eliminated, and the camera sensor may be moved to the position of the tilted intermediate image plane (as described above in connection with the FIG. 2A embodiment). In alternative embodiments, the SLM shown in the FIG. 5A embodiment may also be combined with the cylindrical optical components described above in connection with the FIG. 2A-2C embodiments.

Figure 6G:
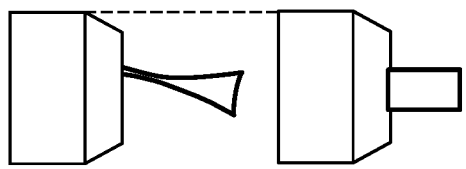
FIG. 6G depicts a light sheet with a Gaussian beam having reduced tilt.
Figure 6F:
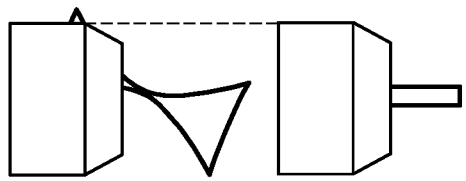
FIG. 6F depicts a light sheet with a high numerical aperture Gaussian beam.
Figure 6E:
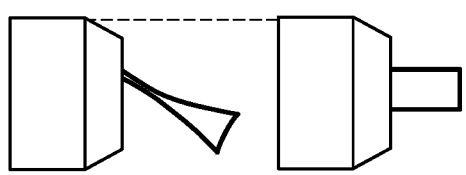
FIG. 6E depicts a light sheet with a low numerical aperture Gaussian beam.

One or more of a wide variety of strategies for modifying the light sheet may be implemented using the SLM 415. For example, the SLM 415 may be designed so that the light sheet (or other illumination pattern) will follow a Bessel beam function or a Bessel comb function (as depicted in FIG. 6B). In alternative embodiments, strategies such as making lines or points at desired locations in the field of view may be used (as depicted in FIG. 6C, which shows a plurality of high NA rows or dots). For example, the points could be vertical or tilted, or they could merge to create a plane or a lumpy plane. The SLM patterns ultimately encode the beam shape. They can act in Fourier space, or as an aperture/beam block.

Figure 6D:
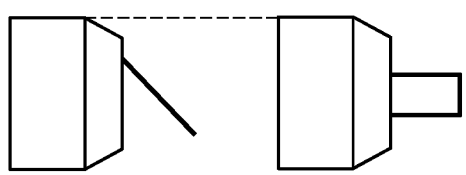
FIG. 6D depicts a light sheet that has been optimized for flatness.
Figure 6C:
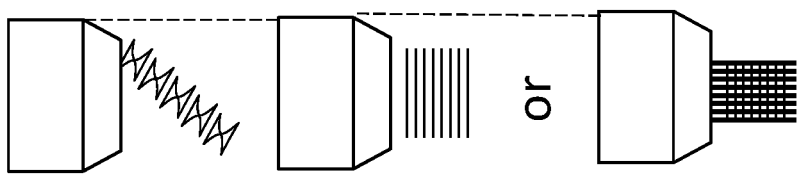
FIG. 6C depicts illumination patterns with a plurality of high NA rows or dots.
Figure 6B:
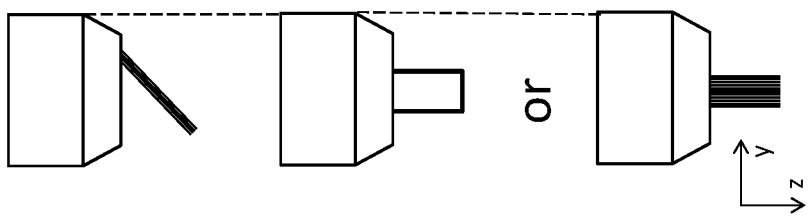
FIG. 6B depicts illumination patterns that follow certain Bessel functions.
Figure 6A:
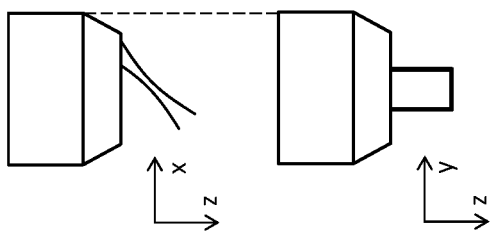
FIG. 6A depicts a light sheet that follows a Gaussian beam function.

In other alternative embodiments, full 3D beam shaping may be implemented to make the sheet as flat as possible over the desired depth (as depicted in FIG. 6D). The SLM 415 can also be used to adjust NA, tilt, lateral length, and the pattern in order to optimize the sheet of light that is projected into the sample for a desired task. For example, the conventional Gaussian beam (depicted in FIG. 6A) can be modified (as seen in FIG. 6E) when the SLM is designed to provide a low NA. Or the beam can be modified (as seen in FIG. 6F) when the SLM is designed to provide a high NA. The SLM 415 may also be used to decrease the tilt of the beam, as seen in FIG. 6G (or, alternatively, to increase the tilt). Alternatively, the SLM can be designed to shift the position of the center of the Gaussian beam.

This SLM-based approach can also be used to enable patterned illumination for structured light in all three dimensions, as well as switching of patterns between frames at high speeds. Although the SLM will add significant cost to the system, these components could enable significant optimization and flexibility without relying on moving parts.

Returning to FIG. 5A, because SLMs can be dynamically controlled, the SLM approach could also be used to refine and optimize alignment of the whole system via feedback on image quality from the camera (or other wavefront/imaging sensor). This could enable dynamic, computer-controlled adjustment of light sheet NA, sheet width, intensity, sheet angle, and position, and also correct for aberrations caused by optical elements and other factors (as in adaptive optics). And notably, all of these adjustments can be implemented without relying on mechanical adjustments.

The SLM 415 can also be used to dynamically adjust the numerical aperture (NA) of the light sheet (and the resolution associated therewith) to enable 'zooming in' on smaller samples or regions of interest, leveraging a narrower light sheet over a reduced depth of field. The sample could then be imaged with fewer camera rows, thus permitting faster frame rates and higher density sampling in the scan direction. Reducing the NA of the light sheet could then extend depth of field, allowing larger regions of interest within the same sample (or a larger sample) to be imaged with a slight sacrifice in light sheet thickness.

The SLM 415 can also be used to improve light efficiency and/or adjust sheet line length to minimize photodamage and accommodate image-splitting. The SLM 415 can also be used to implement automated alignment of the light sheet to the camera image plane. The latter can optionally be implemented in a closed-loop fashion with feedback from the camera to ensure system alignment.

Figure 5B:
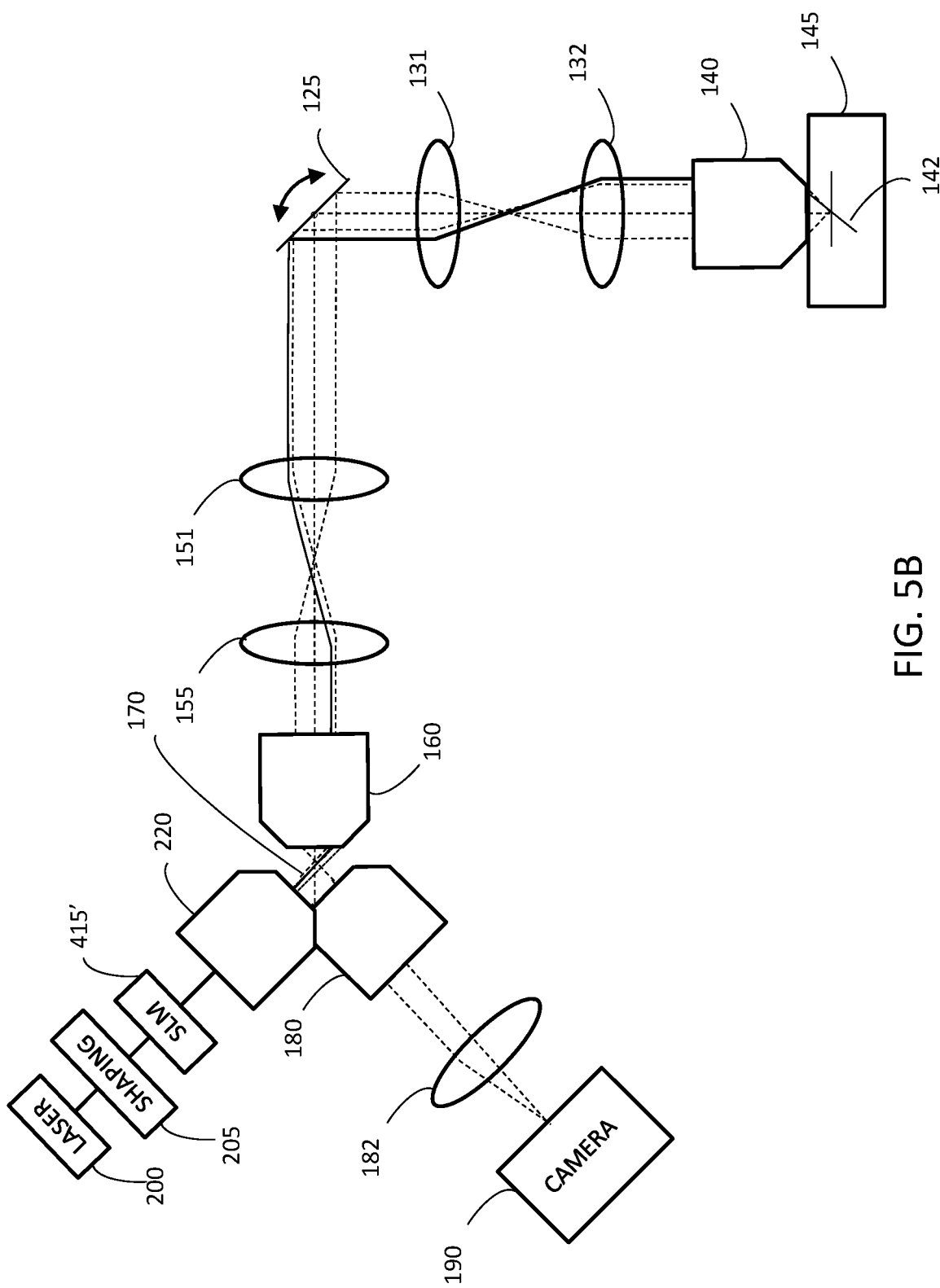
FIG. 5B is a block diagram of an alternative system that incorporates an SLM to optimize the light sheet, in which the sheet of excitation light is injected into the second objective.

FIG. 5B is similar to the FIG. 5A embodiment, except that instead of injecting the sheet of excitation light at the proximal end of the detection arm using a beam splitter, the sheet of excitation light is injected into the distal end of the second set of optical components 151-160, as discussed above in connection with FIG. 2C. When this FIG. 5B configuration is used, the SLM 415' is preferably disposed between the beam shaping optics 205 and the fourth objective 220. The SLM 415' in this embodiment may be used to provide all of the functions associated with the SLM 415 discussed above in connection with the FIG. 5A embodiment.

In alternative embodiments, an SLM also be used for detection-side corrections. In some embodiments, different parts of the same light modulator could be used for both excitation and emission to save costs. Alternatively or additionally, a phase plate may be added immediately behind the first objective in the excitation arm (which would be immediately above the first objective 140 in the FIG. 5A embodiment) in order to further shape the sheet of light 142 that enters the sample 145 to the desired shape.

Section 3: Customized Embodiments for Anatomical Imaging

Figure 7:
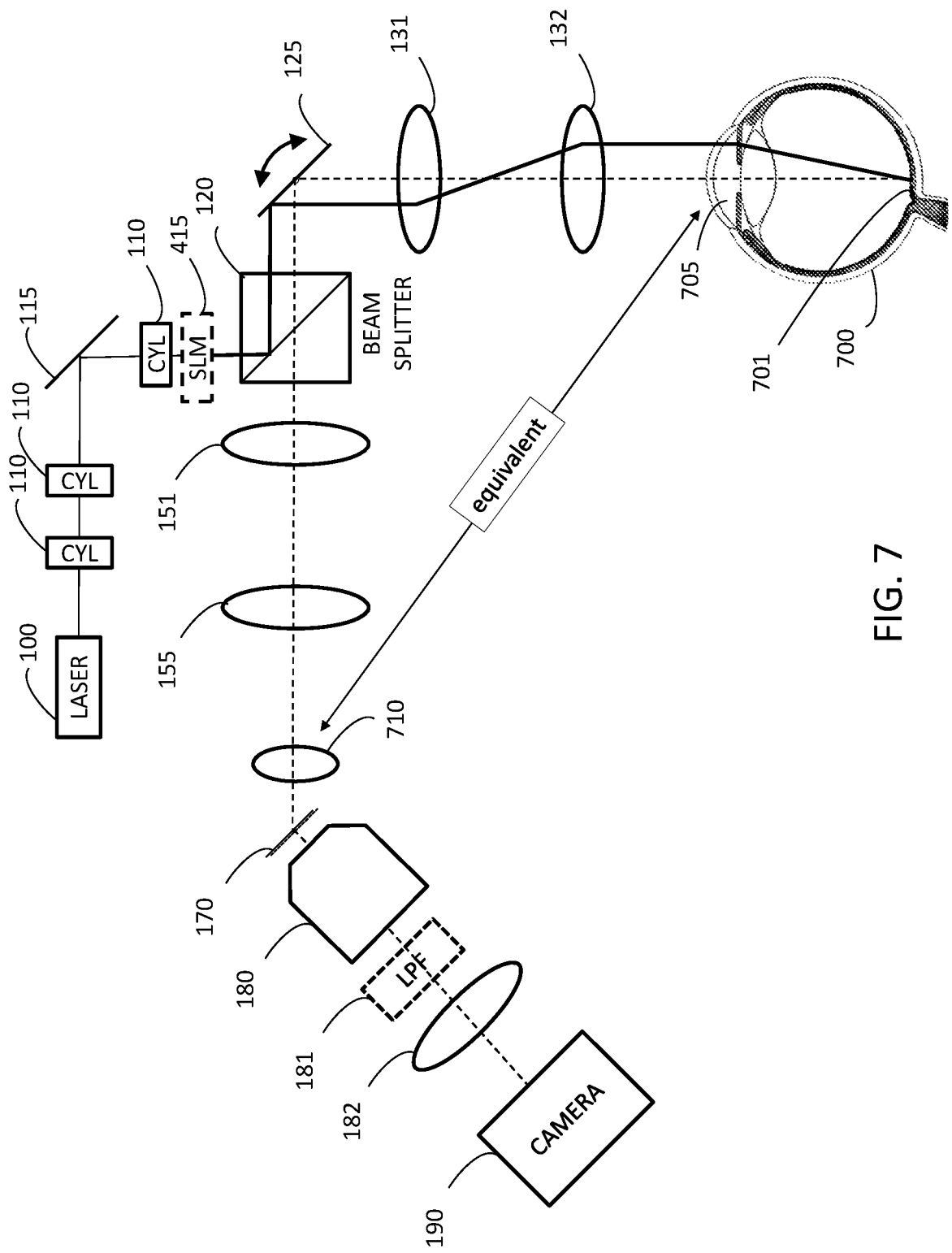
FIG. 7 depicts an embodiment of SCAPE for performing imaging inside an eyeball.

FIG. 7 depicts an alternative embodiment that is customized for performing imaging inside an eyeball 700 (e.g. for imaging the retina 701). As explained above in connection with the FIG. 1 embodiment, significant advantages are obtained when the optics in the excitation arm matches the optics in the detection arm. But when the optics in the excitation arm matches the optics in the detection arm and imaging is being performed on objects within the eyeball 700 that are located behind the lens 705 of the eyeball, that lens 705 of the eye throws the optics in the excitation arm out of balance with the optics in the detection arm. This imbalance eliminates the advantages discussed above. One way to regain these advantages is to rebalance the optics in the detection arm with the optics in the excitation arm by adding an additional lens 710 to the detection arm. This additional lens 710 may be designed to have the same optical characteristics as the lens 705 in the eyeball 700 that is being imaged. The introduction of this lens 710 into the detection path restores balance to the optical system, so that the advantages that flow from a balanced system can be obtained.

In alternative embodiments, the magnification of the detection arm 151, 155, 710 may be lower than the magnification in the excitation arm 131, 132 in order to decrease the tilt of the intermediate image plane 170. Optionally, the asymmetric magnification discussed above in connection with FIG. 2A-2C may be combined with the objectiveless design of this FIG. 7 embodiment.

Because this FIG. 7 embodiment uses the lens 705 of the eye in place of the objective (140 in the FIG. 1 embodiment), the NA of this embodiment will be relatively low. Nevertheless, while the reduced NA will dramatically degrade sectioning, it will not remove sectioning completely, and a depth resolved image of the retina can still be obtained.

Optionally, optical coherence tomography (OCT) imaging of the eye 700 may be implemented using the same components depicted in FIG. 7. In some embodiments, SCAPE imaging and OCT imaging may even be implemented simultaneously by using a blue laser for the SCAPE imaging and a red laser for the OCT imaging.

Note that in alternative embodiments, the components 180-182 that sit between the tilted intermediate image plane and the camera 190 may be eliminated, and the camera sensor may be moved to the position of the tilted intermediate image plane (as described above in the FIG. 2A embodiment). In alternative embodiments, the SLM shown in the FIG. 5A/5B embodiment may also be combined with the cylindrical optical components described above in connection with the FIG. 2A embodiment.

Figure 8:
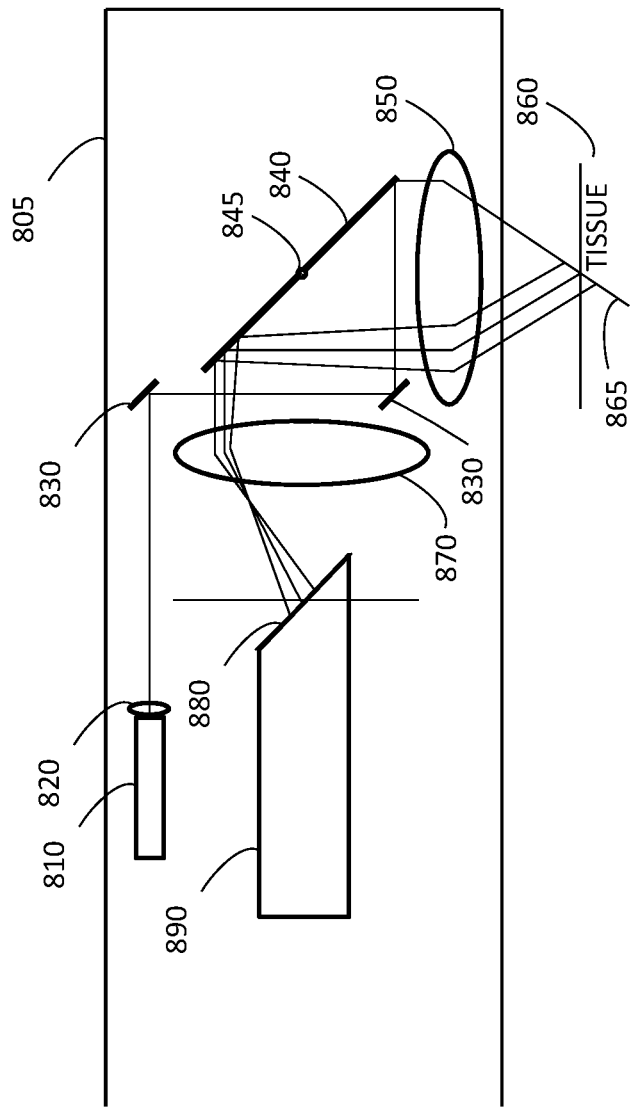
FIG. 8 depicts a miniaturized embodiment of SCAPE.

FIG. 8 depicts a miniaturized embodiment designed to fit within the confines of a catheter 805 that measures between 2 and 10 mm in diameter in some embodiments, or between 2 and 5 mm in diameter. In the illustrated embodiment, excitation light arrives via a fiber optic 810 and a mini lens 820 conditions the output of the fiber optic 810 to form a sheet of light. GRIN lenses may be used for this purpose. Optionally, a linear bundle may be used to tune the sheet width and/or the NA via the illumination at the proximal end of the fiber bundle. The light that exits the mini lens 820 will be a sheet of light. This sheet of light is directed by mirrors 830 onto a scanning mirror 840.

The scanning mirror 840 may be implemented using a MEMS scanner that oscillates around the illustrated center point 845 to make a scan pattern. The scan pattern will cause the illumination beam to pass through lens 850 and into the tissue 860 and form a sheet of light 865 within the tissue. The position of the sheet of light 865 within the tissue will depend on the angle of the scanner 840. The tissue will emit fluorescent light, and this fluorescent light is collected by lens 850 and routed back to the scanner 840. From there it is directed through lens 870 to form a tilted image plane 880.

In some embodiments, a camera sensor is positioned at this tilted image plane 880. In these embodiments, the camera sensor is preferably a two dimensional camera sensor with small pixels (e.g. on the order of 1 µm). Signals from the camera sensor 880 are electrically transmitted out of the catheter 805 for processing by an image processor (not shown).

In alternative embodiments, the image at the tilted image plane 880 may be transmitted out of the catheter 805 via a fiber-optic bundle 890 with a beveled input edge that is angled to match the tilt of the tilted image plane 880. This fiber-optic bundle 890 relays the image from the tilted image plane 880 to a camera located at the proximal end of the catheter 805. In some embodiments, the fibers in the bundle 890 are tapered to terminate at a camera with large pixels (e.g. 7 µm×7 µm) located at the proximal end of the catheter. Coarse images could be obtained using a bundle of fibers that contains a 50×250 bundle. Higher-resolution images can be obtained if more fibers are used e.g. 100×500 fibers or more.

The imaging apparatus of FIG. 8 may be implemented using a catheter 805 and a first lens 850 disposed at a distal end of the catheter. The first lens 850 has an inner surface. A scanning mirror 840 scans a sheet of light towards the inner surface of the first lens 850. The first lens 840 routes light arriving from the scanning mirror 840 into tissue 860 located outside the catheter 805, and routes fluorescent light generated in the tissue 860 back towards the scanning mirror 840. The scanning mirror 840 reflects the fluorescent light that arrives via the first lens 850 in a first direction. A second lens 870 is disposed in front of the scanning mirror 840 in the first direction, and the second lens 870 is positioned to accept the fluorescent light that was reflected by the scanning mirror 840. The second lens 870 routes the fluorescent light received from the scanning mirror 840 onto a tilted intermediate image plane 880. A camera is optically positioned to capture images at the tilted intermediate image plane 880.

In these embodiments, the sheet of light may optionally be generated by a laser and a GRIN lens 820 and/or a laser and a fiber optic bundle 810.

In these embodiments, the camera may optionally comprise a 2D image sensor positioned at the tilted intermediate image plane 880. Alternatively, the camera may optionally comprise a 2D image sensor positioned at a position that is remote from the tilted intermediate image plane 880, plus a fiber optic bundle 890 that routes light from the tilted intermediate image plane 880 to a remote 2D image sensor.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An imaging apparatus comprising:
   a first set of optical components having a proximal end and a distal end, wherein the first set of optical components includes an objective disposed at the distal end of the first set of optical components;
   a second set of optical components having a proximal end and a distal end, wherein the second set of optical components includes an objective disposed at the distal end of the second set of optical components, wherein the second set of optical components has a first magnification in a first radial direction and a second magnification in a second radial direction that is perpendicular to the first radial direction, and wherein the first magnification is at least 1.5 times the second magnification;
   a scanning element that is disposed proximally with respect to the proximal end of the first set of optical components and proximally with respect to the proximal end of the second set of optical components,
      wherein the scanning element is arranged to route a sheet of excitation light so that the sheet of excitation light will pass through the first set of optical components in a proximal to distal direction and project into a sample that is positioned distally beyond the distal end of the first set of optical components, wherein the sheet of excitation light is projected into the sample at an oblique angle, and wherein the sheet of excitation light is projected into the sample at a position that varies depending on an orientation of the scanning element,
      wherein the first set of optical components routes detection light from the sample in a distal to proximal direction back to the scanning element, and
      wherein the scanning element is also arranged to route the detection light so that the detection light will pass through the second set of optical components in a proximal to distal direction and form an intermediate image plane at a position that is distally beyond the distal end of the second set of optical components; and
   a light detector array arranged to capture images of the intermediate image plane.

2. The apparatus of claim 1, wherein the intermediate image plane is stationary.

3. The apparatus of claim 1, wherein the detection light arriving from the sample has a depth dimension and a width dimension that is perpendicular to the depth dimension,
   wherein the magnification in the first radial direction in the second set of optical components corresponds to magnification of the width dimension of the detection light,
   wherein the first set of optical components has a uniform magnification in all radial directions, and
   wherein the uniform magnification of the first set of optical components is the same as the second magnification of the second set of optical components.

4. The apparatus of claim 3, wherein the first magnification is at least 2 times the second magnification.

5. The apparatus of claim 4, wherein the first set of optical components comprises a first set of spherical optical components, and wherein the second set of optical components comprises (a) a second set of spherical optical components with a magnification that matches the first set of spherical optical components and (b) a set of cylindrical optical components.

6. The apparatus of claim 1, wherein the detection light arriving from the sample has a depth dimension and a width dimension that is perpendicular to the depth dimension, and wherein the magnification in the first radial direction in the second set of optical components corresponds to magnification of the width dimension of the detection light.

7. The apparatus of claim 6, wherein the light detector array comprises a 2D image sensor with pixels arranged in a plurality of readout rows, and the light detector array is oriented so that each of the plurality of readout rows corresponds to a respective different position in the depth direction of the detection light.

8. The apparatus of claim 6, wherein the light detector array comprises a 2D image sensor with pixels arranged in a plurality of readout rows, and the light detector array is oriented so that each of the plurality of readout rows corresponds to a respective different position in the depth direction of the detection light, and
   wherein the captured images of the intermediate image plane are arranged in frames, and each frame includes data from not more than half of the rows.

9. The apparatus of claim 8, wherein each frame includes data from not more than one quarter of the rows.

10. A method of imaging a sample comprising:
    projecting a sheet of excitation light into a sample, wherein the sheet of excitation light is projected into the sample at an oblique angle, and wherein the sheet of excitation light is projected into the sample at a position that varies with time;
    routing detection light arriving from the sample into a proximal end of an optical system that has a first magnification in a first radial direction and a second magnification in a second radial direction that is perpendicular to the first radial direction, wherein the first magnification is at least 1.5 times the second magnification;
    forming a stationary intermediate image plane at a distal end of the optical system; and
    capturing images of the intermediate image plane at a plurality of times.

11. The method of claim 10, wherein the detection light arriving from the sample has a depth dimension and a width dimension that is perpendicular to the depth dimension, and wherein the magnification in the first radial direction in the optical system corresponds to magnification of the width dimension of the detection light.

12. The method of claim 10, wherein the first magnification is at least 2 times the second magnification.

13. The method of claim 10, wherein the sheet of excitation light is projected into the sample at a position that varies with time depending on an orientation of a scanning element,
    wherein the routing step is implemented by the scanning element, and wherein each of the images of the intermediate image plane corresponds to a different orientation of the scanning element.

14. An imaging apparatus comprising:
a first set of optical components having an objective, wherein the first set of optical components is arranged to (a) route excitation light into the objective so as to generate a sweeping sheet of excitation light through the objective and (b) simultaneously route image light returning through the objective along a detection path;
a second set of optical components disposed in the detection path arranged to receive light from the first set of optical components and produce an asymmetrically magnified oblique real image by magnifying in a first radial direction at a power of at least 1.5 times that in a second radial direction perpendicular to the first radial direction; and
a light detector array positioned to sample the oblique real image.

15. The apparatus of claim 14, wherein the oblique real image has a first dimension whose pixels resolve light from multiple depths along an optical axis in front of the objective and a second dimension perpendicular the first dimension whose pixels resolve light from multiple positions along an axis transverse to the optical axis.

16. The apparatus of claim 14, wherein the second set of optical components produce the asymmetrically magnified image by magnifying in the first radial direction at a power of at least 2 times that in the second radial direction.

17. The apparatus of claim 14, wherein the detection path includes a scanning element that routes the image light from the first set of optical components into the second set of optical components, wherein the scanning element also routes the sheet of excitation light into the first set of optical components.

18. The apparatus of claim 17, wherein the first set of optical components provides symmetric magnification between the objective and the scanning element.

19. The apparatus of claim 14, wherein the light detector array comprises a 2D image sensor.

20. The apparatus of claim 19, further comprising a sampling controller that reads out the pixels of the light detector array row by row, wherein the rows correspond to the second dimension.

21. The apparatus of claim 20, wherein the sampling controller reads out only a fraction of the total number of rows of the light detector array for each of position of the scanning element.

* * * * *